United States Patent [19]

Sabesan

[11] Patent Number: 5,220,008

[45] Date of Patent: Jun. 15, 1993

[54] OLIGOSACCHARIDE INHIBITORS FOR INFLUENZA VIRUS

[75] Inventor: Subramaniam Sabesan, Wilmington, Del.

[73] Assignee: E. I. du Pont de Nemours and Company, Wilmington, Del.

[21] Appl. No.: 796,201

[22] Filed: Nov. 22, 1991

[51] Int. Cl.$^5$ .................. C07H 15/00; C07H 15/06; A61K 31/70
[52] U.S. Cl. ........................ 536/4.1; 536/53; 536/55.1; 536/55.2; 536/17.9; 536/119; 527/300
[58] Field of Search ............ 536/4.1, 55.1, 55.2, 536/53, 17.9, 119

[56] References Cited

U.S. PATENT DOCUMENTS

| | | | |
|---|---|---|---|
| 4,767,845 | 8/1988 | Lemieux et al. | 536/53 |
| 5,030,723 | 7/1991 | Nudelman et al. | 536/53 |
| 5,032,505 | 7/1991 | Pierce et al. | 536/53 |
| 5,079,353 | 1/1992 | Ratcliffe et al. | 536/55.1 |

OTHER PUBLICATIONS

Sabesan et al., *J. Am. Chem. Soc.*, 113, 5865–5866 (1991).
Sabesan et al., *J. Am. Chem. Soc.*, 108, 2068–2080 (1986).
Spaltenstein et al., *J. Am. Chem. Soc.*, 113, 686–687 (1991).
Paulson et al., *J. Bio. Chem.*, 252, 2363–2371 (1977).
Glick et al., *J. Am. Chem. Soc.*, 113, 4701–4703 (1991).
Unverzagt et al., *J. Am. Chem. Soc.*, 112, 9308–9309 (1990).
Weis et al., *Nature*, 333, 426–431 (1988).
Paulson et al., *Pure & Appl. Chem.*, 56, 797–805 (1984).
Pritchett et al., *J. Biol. Chem.*, 264, 17, 9850–9858 (1989).

*Primary Examiner*—Ronald W. Griffin

[57] ABSTRACT

Heptasaccharides containing bivalent receptor determinants for the influenza virus of human isolates which inhibit binding of the virus to host cells as well as other saccharides used in preparation of the heptasaccharides are provided.

15 Claims, 2 Drawing Sheets

OLIGOSACCHARIDE INHIBITORS FOR INFLUENZA VIRUS

FIELD OF THE INVENTION

The present invention relates to heptasaccharides containing bivalent receptor trisaccharide determinants that bind the influenza virus of human isolates and which exhibit increased inhibitory potency.

BACKGROUND OF THE INVENTION

Influenza virus binds to the erythrocytes through attachment to cell surface carbohydrates. Specifically, influenza virus envelope protein called hemagglutinin binds to a trisaccharide structure containing sialic acid, galactose and N-acetylglucosamine, and is present as the terminal structure of large carbohydrate units of cell surface glycoproteins and glycolipids. This binding is crucial for viral infection. The design of molecules containing carbohydrate structures that mimick the structures recognized by the hemagglutinin molecules and preferentially bind to the virus should inhibit the influenza virus infection. Thus such molecules may prove to be useful drugs.

In biological systems, the receptor (the hemagglutinin on the virus envelope) and the receptor ligands (the cell surface carbohydrates) are displayed in multiple copies. As a result, the interaction between a virus and the erythrocyte involves multipoint attachments between the receptor and receptor ligands. This is hard to mimick with synthetic molecules. For example, the hemagglutinins present on the influenza virus exist as trimers with three potential binding sites and also in multiple copies. Therefore the synthetic inhibitors should be capable of binding not only to the three binding sites of a single hemagglutinin trimer, but also to the adjacent hemagglutinin molecules as well.

Binding to the adjacent hemagglutinin molecules can be achieved by immobilization of sialic acid structures on a polymer back bone as has been shown, Spaltenstein et al., *Am. Chem. Soc.*, 113, 686–687 (1991). An optimum distance of 55A was proposed for optimum binding by Glick et al, *J. Am. Chem. Soc.*, 113, 4701–4703 (1991). However, these two studies dealt with the preparation of compounds containing only one sugar, namely, the sialic acid. However, studies by Paulson et al, *J. Biol. Chem.*, 264, 9850–9859 (1989) showed that in addition to the sialic acid, other sugars, namely, the galactose and N-acetylglucosamine that are connected to the sialic acid are also important for viral recognition.

Sabesan et al., *J. Am. Chem. Soc.*, Vol. 108, pp. 2068–2080 (1986) teach the combined chemical and enzymatic synthesis of ten sialyloligosaccharides that occur as terminal sequences in glycoproteins and glycolipids. Sabesan et al., *J. Am. Chem. Soc.*, 113, 5865–5866 (1991), disclose demonstration of increased inhibitor potency by low molecular weight, synthetic, bivalent receptor determinants containing the trisaccharide structures for the influenza virus of human isolates. The importance of cluster oligosaccharide effects for binding toward proteins is exemplified.

Spaltenstein et al., *J. Am. Chem. Soc.*, Vol. 113, pp. 686–687 (1991) have prepared polymers containing a cluster of sialic acids by polymerization of acrylic esters of sialosides. It was concluded that polyvalent derivatives of sialic acid are more effective than monomeric ones in inhibiting hemagglutination.

The present invention relates to the design of a hemagglutinin recognition molecule wherein two identical trisaccharide structures (bivalent structures) comprising sialic acid (N-acetylneuraminic acid), galactose, and N-acetylglucosamine are attached to another sugar molecule (anchoring sugar). The bivalent structures are better inhibitors of influenza virus than the monovalent structures. Also, the anchoring sugar has been pended with a functional group that upon modification can be polymerized to a macromolecule capable of inhibiting influenza virus infection.

SUMMARY OF THE INVENTION

The present invention provides heptasaccharide compounds which exhibit increased inhibitory potency to influenza virus of human isolates when compared to synthetic monovalent sialosides. These heptasaccharide compounds contain bivalent receptor trisaccharide determinants. They demonstrate preferential binding to influenza virus particles and inhibit binding of the virus particles to human host cells. The present invention also provides trisaccharide and pentasaccharide compounds used in the preparation of the above heptasaccharides.

The present invention provides a compound comprising the formula I, II, III, IV, V or VI wherein $R^1$ is $(CH_2)_nCOOR^2$ or $(CH_2)_nCONHR^3NH$-$C(O)R^4$, n is 1 to 20; $R^2$ is a $C_1$ to $C_6$ alkyl or aralkyl; $R^3$ is $C_1$ to $C_4$ alkyl; $R^4$ is $OCH_2C_6H_5$ or O-alkenyl; $R^5$, $R^6$, $R^7$ and $R^8$ are each independently H, $C_6H_5CH_2$, alkyl or tertbutyldimethylsilyl; and R is a monosaccharide selected from the group consisting of glucosamine and its N- or O-protected equivalents, a disaccharide consisting of galactose glycosidically linked to N-acetylglucosamine or a trisaccharide consisting of N-acetylneuraminic acid glycosidically linked to galactose which in turn is glycosidically linked to N-acetylglucosamine.

The present invention further comprises a compound comprising the formula

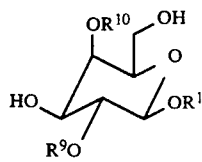

VII wherein $R^1$ is as defined above, $R^9$ is a trisaccharide consisting of N-acetylneuraminic acid glycosidically linked to galactose which in turn is glycosidically linked to N-acetylglucosamine; and $R^{10}$ is a disaccharide consisting of galactose glycosidically linked to N-acetylglucosamine.

The present invention further comprises a compound comprising the formula

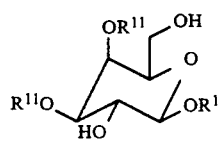

VIII wherein $R^1$ is as defined above and each $R^{11}$ is independently a monosaccharide selected from the group consisting of glucosamine and its N- and/or O-protected equivalents, or a disaccharide consisting of galactose glycosidically linked to N-acetylglucosamine.

DETAILED DESCRIPTION OF THE INVENTION

The present invention comprises heptasaccharide compounds which exhibit increased inhibitory potency to influenza virus of human isolates when compared to synthetic monovalent sialosides. The present invention further comprises other saccharide compounds used in the preparation of these heptasaccharides. The heptasaccharide compounds contain bivalent receptor trisaccharide determinants which demonstrate preferential binding to influenza virus of human isolates, thereby inhibiting binding of the virus particles to human host cells. The heptasaccharides can be polymerized to provide a polymeric inhibitor.

The influenza virus binds via its hemmagglutinins to a trisaccharide residue present on the host cell and this has been recognized as a key event in the infection processes. It is known that the hemagglutinin molecules have the potential to bind both intra and intermolecularly to the cell surface carbohydrates. It is important to understand the carbohydrate structural requirements for such binding. It has been found that the distance between the end sialic acid residues in the bivalent receptor structures affect the binding efficiency. Thus the attachment position of the trisaccharide groups in the heptasaccharide molecule which determines the distance between the end units conformationally, affects the inhibition potentency.

The compounds of the present invention comprise trisaccharides, pentasaccharides and heptasaccharides of formula I, II, III, IV, V, VI, VII, and VIII as defined above.

Preferred compounds of this invention include those numbered 2, 4, 6 to 8 and 15 to 31 in the following Structure Schemes A, B, C, D and E. The numbers assigned to the compounds correspond to the Examples hereinafter. Thus the synthesis details for each preferred compound can be found in the Example of the corresponding number.

For the following Structure Schemes A, B, C, D and E, the following abbreviations are used:

$R_1$ is 5-(methoxycarbonyl)pentyl;
Ph is phenyl;
tBDMS, is tertbutyldimethylsilyl;
Bz is benzoyl; and
Ac is acetyl.

STRUCTURE SCHEME A
MONOSACCHARIDE INTERMEDIATES

1

2

3

4

5

6

Figure 1B:
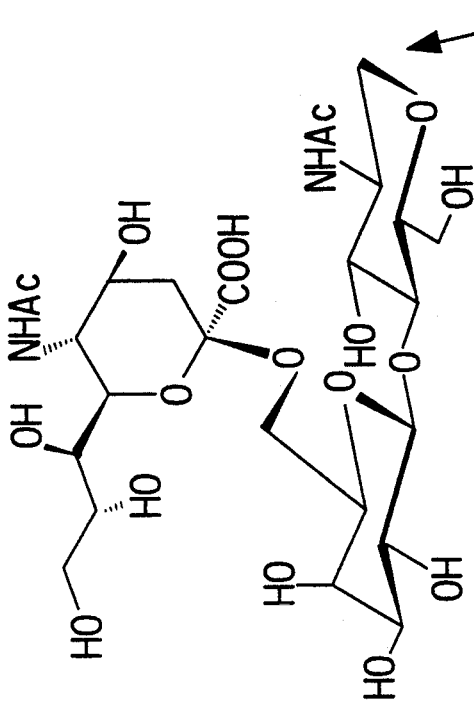
FIGS. 1A, 1B and 1C each depict one of the possible structures of the heptasaccharides containing bivalent receptor trisaccharide determinants. Groups A and B can be bonded at the carbon designated by the arrow to any two of the oxygens at positions 2, 3, 4 or 6 of Group C.
Figure 1C:
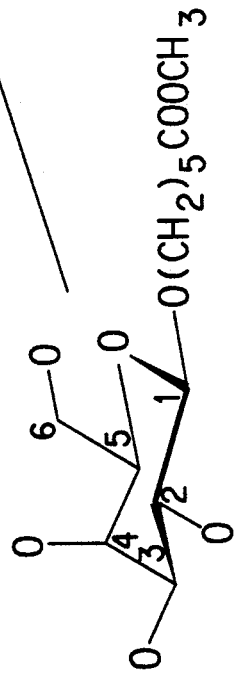
Figure 1A:
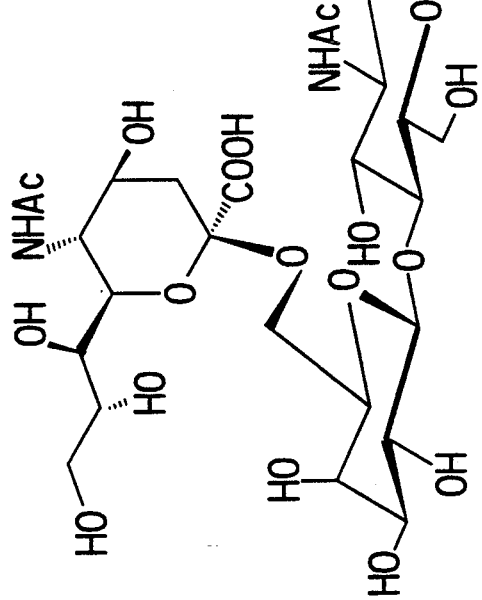
Figure 2:
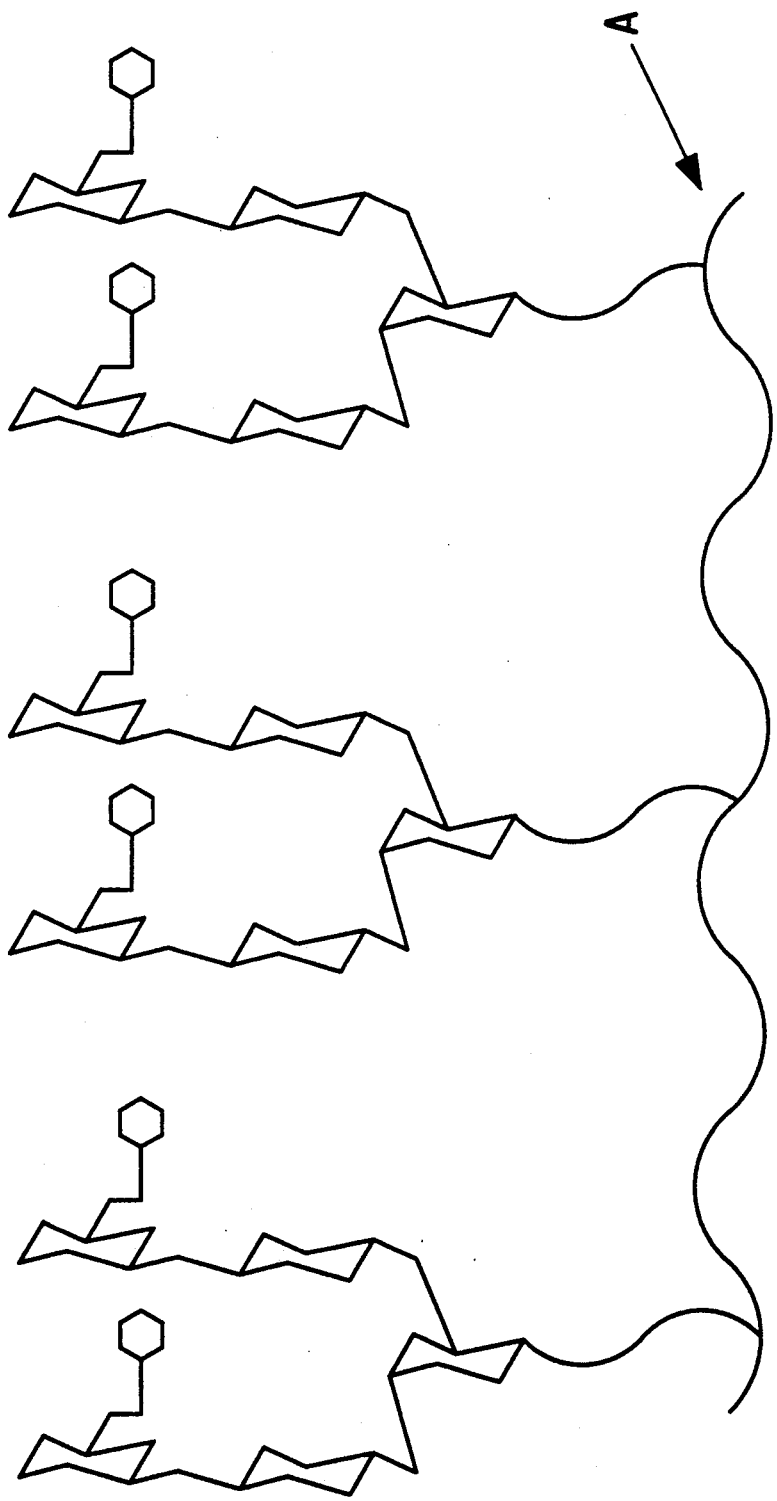
FIG. 2 depicts a design of a polymeric heptasaccharide inhibitor wherein A represents the polymeric backbone.

-continued
STRUCTURE SCHEME A
MONOSACCHARIDE INTERMEDIATES
-continued
STRUCTURE SCHEME B
TRISACCHARIDE INTERMEDIATES*
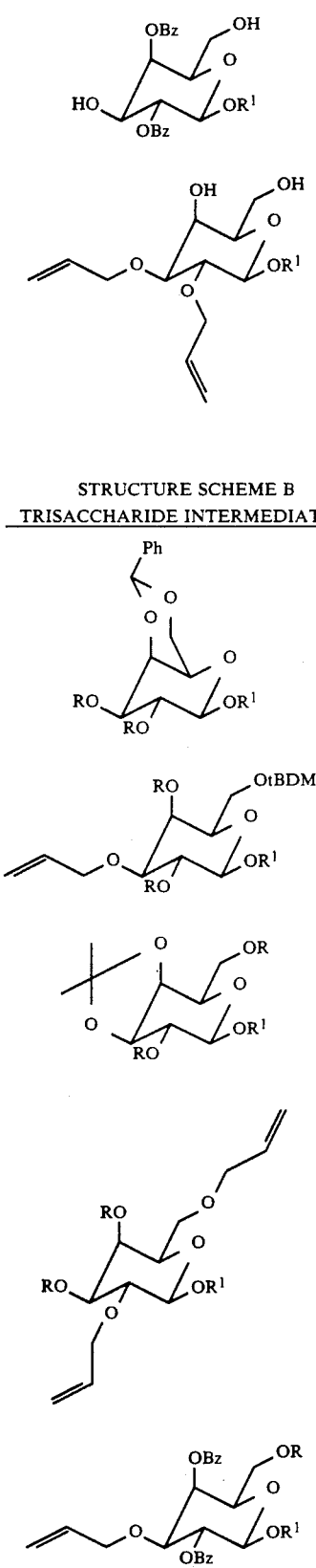
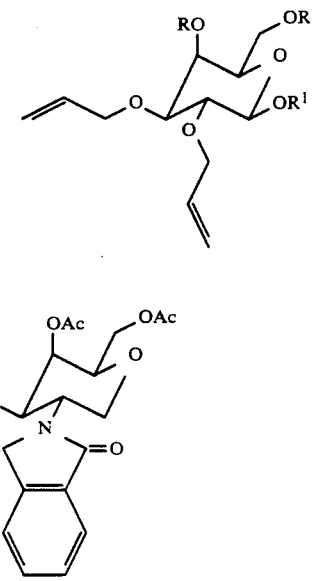
STRUCTURE SCHEME C
TRISACCHARIDE INTERMEDIATES*
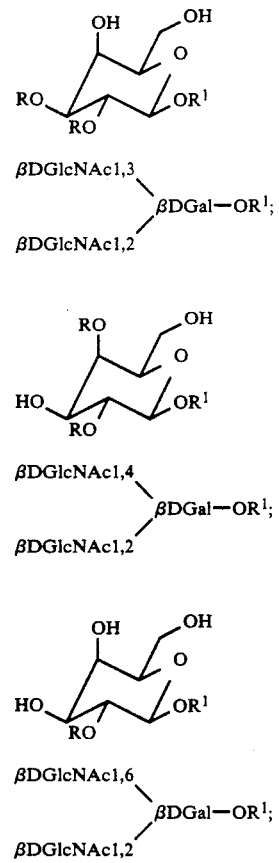

STRUCTURE SCHEME C
TRISACCHARIDE INTERMEDIATES*

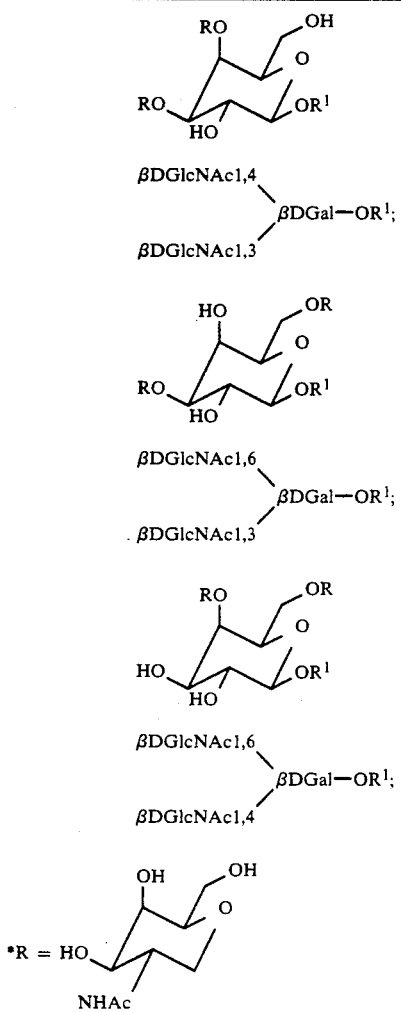

18  βDGlcNAc1,4
        \
         βDGal—OR¹;
        /
    βDGlcNAc1,3

19  βDGlcNAc1,6
        \
         βDGal—OR¹;
        /
    βDGlcNAc1,3

20  βDGlcNAc1,6
        \
         βDGal—OR¹;
        /
    βDGlcNAc1,4

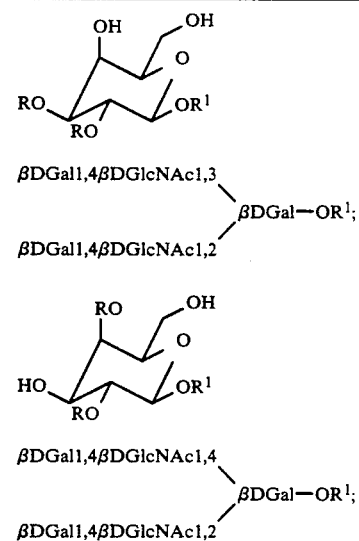

*R =

STRUCTURE SCHEME D
PENTASACCHARIDE INTERMEDIATES*

21  βDGal1,4βDGlcNAc1,3
              \
               βDGal—OR¹;
              /
    βDGal1,4βDGlcNAc1,2

22  βDGal1,4βDGlcNAc1,4
              \
               βDGal—OR¹;
              /
    βDGal1,4βDGlcNAc1,2

STRUCTURE SCHEME D
PENTASACCHARIDE INTERMEDIATES*

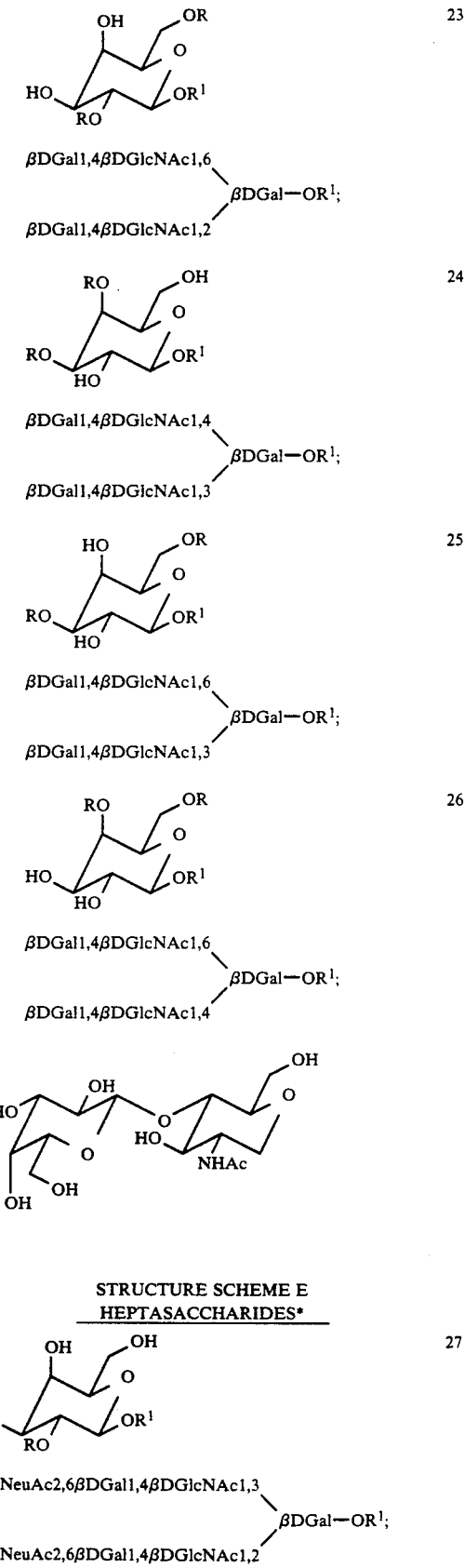

23  βDGal1,4βDGlcNAc1,6
              \
               βDGal—OR¹;
              /
    βDGal1,4βDGlcNAc1,2

24  βDGal1,4βDGlcNAc1,4
              \
               βDGal—OR¹;
              /
    βDGal1,4βDGlcNAc1,3

25  βDGal1,4βDGlcNAc1,6
              \
               βDGal—OR¹;
              /
    βDGal1,4βDGlcNAc1,3

26  βDGal1,4βDGlcNAc1,6
              \
               βDGal—OR¹;
              /
    βDGal1,4βDGlcNAc1,4

*R =

STRUCTURE SCHEME E
HEPTASACCHARIDES*

27  αDNeuAc2,6βDGal1,4βDGlcNAc1,3
                          \
                           βDGal—OR¹;
                          /
    αDNeuAc2,6βDGal1,4βDGlcNAc1,2

-continued
STRUCTURE SCHEME E
HEPTASACCHARIDES*

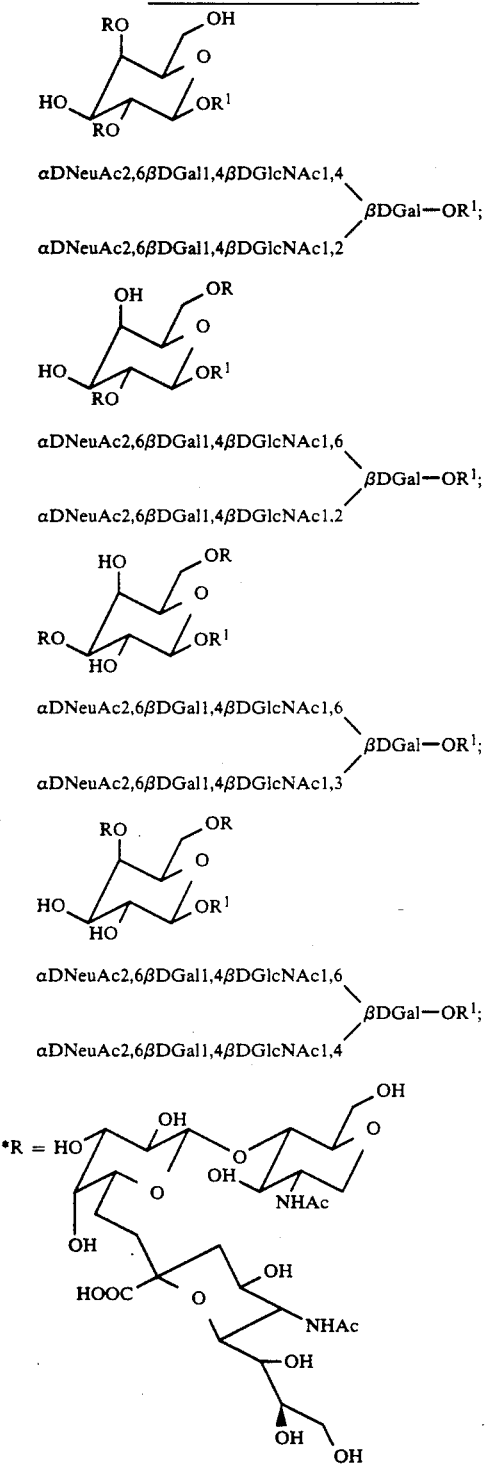

28
αDNeuAc2,6βDGal1,4βDGlcNAc1,4\
  βDGal—OR¹;
αDNeuAc2,6βDGal1,4βDGlcNAc1,2/

29
αDNeuAc2,6βDGal1,4βDGlcNAc1,6\
  βDGal—OR¹;
αDNeuAc2,6βDGal1,4βDGlcNAc1,2/

30
αDNeuAc2,6βDGal1,4βDGlcNAc1,6\
  βDGal—OR¹;
αDNeuAc2,6βDGal1,4βDGlcNAc1,3/

31
αDNeuAc2,6βDGal1,4βDGlcNAc1,6\
  βDGal—OR¹;
αDNeuAc2,6βDGal1,4βDGlcNAc1,4/

Preferred compounds of formula I include trisaccharide 15, pentasaccharide 21, and heptasaccharide 27. Trisaccharide 15 is 5-(methoxycarbonyl)pentyl 2,3-di-O-(2-acetamido-2-deoxy-β-D-glucopyranosyl)-β-D-galactopyranoside. Pentasaccharide 21 is 5-(methoxycarbonyl)pentyl 2,3,-di-O-{β-D-galactopyranosyl(1→4)-2-acetamido-2-deoxy-β-D-glucopyranosyl}-β-D-galactopyranoside. Heptasaccharide 27 is 5-(methoxycarbonyl)pentyl 2,3-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

Preferred compounds of formula II include trisaccharide 16, pentasaccharide 22, and heptasaccharide 28. Trisaccahride 16 is 5-(methoxycarbonyl)pentyl 2,4-di-O-(2-acetamido-2-deoxy-β-D-glucopyranosyl)-β-D-galactopyranoside. Pentasaccharide 22 is 5-(methoxycarbonyl)pentyl 2,4-di-O-{β-D-galactopyranosyl(1→4)-2-acetamido-2-deoxy-β-D-glucopyranosyl}-β-D-galactopyranoside. Heptasaccharide 28 is 5-(methoxycarbonyl)pentyl 2,4-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

Preferred compounds of formula III include trisaccharide 17, pentasaccharide 23, and heptasaccharide 29. Trisaccharide 17 is 5-(methoxycarbonyl)pentyl 2,6-di-O-(2-acetamido-2-deoxy-β-D-glucopyranosyl)-β-D-galactopyranoside. Pentasaccharide 23 is 5-(methoxycarbonyl)pentyl 2,6-di-O-{β-D-galactopyranosyl(1→4)-2-acetamido-2-deoxy-β-D-glucopyranosyl}-β-D-galactopyranoside. Heptasaccharide 29 is 5-(methoxycarbonyl)pentyl 2,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

Preferred compounds of formula IV include trisaccharide 19, pentasaccharide 25, and heptasaccharide 30. Trisaccharide 19 is 5-(methoxycarbonyl)pentyl 3,6-di-O-(2-acetamido-2-deoxy-β-D-glucopyranosyl)-β-D-galactopyranoside. Pentasaccharide 25 is 5-(methoxycarbonyl)pentyl 3,6-di-O-{β-D-galactopyranosyl(1→4)-2-acetamido-2-deoxy-β-D-glucopyranosyl}-β-D-galactopyranoside. Heptasaccharide 30 is 5-(methoxycarbonyl)pentyl 3,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

Preferred compounds of formula V include trisaccharide 20, pentasaccharide 26 and heptasaccharide 31. Trisaccharide 20 is 5-(methoxycarbonyl)pentyl 4,6-di-O-(2-acetamido-2-deoxy-β-D-glucopyranosyl)-β-D-galactopyranoside. Pentasaccharide 26 is 5-(methoxycarbonyl)pentyl 4,6-di-O-{β-D-galactopyranosyl(1→4)-2-acetamido-2-deoxy-β-D-glucopyranosyl}-β-D-galactopyranoside. Heptasaccharide 31 is 5-(methoxycarbonyl)pentyl 4,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

Preferred compounds of formula VI include monosaccharides 2, 4, 6, 7 and 8. Monosaccharide 2 is 5-(methoxycarbonyl)pentyl 3-O-allyl-β-D-galactopyranoside. Monosaccharide 4 is 5-(methoxycarbonyl)pentyl 3-O-allyl-6-O-(t-butyldimethylsilyl)-β-D-galactopyranoside. Monosaccharide 6 is 5-(methoxycarbonyl)pentyl 2,6-di-O-allyl-β-D-galactopyranoside. Monosaccharide 7 is 5-(methoxycarbonyl)pentyl 2,4-di-O-benzoyl-β-D-galactopyranoside. Monosaccharide 8 is 5-(methoxycarbonyl)pentyl 2,3-di-O-allyl-β-D-galactopyranoside.

Preferred compounds of formula VI also include protected trisaccharides 9, 10, 11, 12, 13 and 14. Trisaccharide 9 is 5-(methoxycarbonyl)pentyl 4,6-O-benzylidene-2,3-di-O-(2-deoxy-3,4,6-tri-O-acetyl-2-phthalimido-β-D-glucopyranosyl)-β-D-galactopyranoside. Trisaccharide 10 is 5-(methoxycarbonyl)pentyl 3-O-allyl-6-O-(t-butyldimethylsilyl)-2,4-di-O-(2-deoxy-3,4,6-tri-O-acetyl-2-phthalimido-β-D-glucopyranosyl)-β-D-galactopyranoside. Trisaccharide 11 is 5-(methoxycarbonyl)pentyl 2,6-di-O-(2-deoxy-3,4,6-tri-O-acetyl-2-phthalimido-β-D-glucopyranosyl)-3,4-O-isopropylidene-β-D-galactopyranoside. Trisaccharide 12 is 5-(methoxycarbonyl)pentyl 2,6-di-O-allyl-3,4-di-O-(2-deoxy-3,4,6-tri-O-acetyl-2-phthalimido-β-D-glycopyranosyl)-β-D-galactopyranoside. Trisaccharide 13 is 5-(methoxycarbonyl)pentyl 2,4-di-O-benzoyl-3,6-di-O-(2-deoxy-3,4,6-tri-O-acetyl-2-phthalimido-β-D-glucopyranosyl)-β-D-galactopyranoside. Trisaccharide 14 is 5-(methoxycarbonyl)pentyl 2,3-di-O-allyl-4,6-di-O-(2-deoxy-3,4,6-tri-O-acetyl-2-phthalimido-β-D-glucopyranosyl)-β-D-galactopyranoside.

Preferred compounds of formula VII include 5-(methoxycarbonyl)pentyl 2-O-[5-acetamido-3,5-dideoxy-D-glycero-D-galactononulopyranosylonic acid (2→6)-β-D-galactopyranosyl-(1→4)-2-acetamido-2-deoxy-D-glycopyranosyl]-4-O-[β-D-galactopyranosyl-(1→4)-2-acetamido-2-deoxy-D-glucopyranosyl]-β-D-galactopyranoside (28A).

Preferred compounds of formula VIII are trisaccharide 18 and pentasaccharide 24. Trisaccharide 18 is 5-(methoxycarbonyl)pentyl 3,4-di-O-(2-acetamido-2-deoxy-β-D-glucopyranosyl)-β-D-galactopyranoside. Pentasaccharide 24 is 5-(methoxycarbonyl)pentyl 3,4-di-O-{ β-D-galactopyyranosyl(1→4)-2-acetamido-2-deoxy-β-D-glucopyranosyl}-β-D-galactopyranoside.

Especially preferred compounds of the present invention are the heptasaccharides 27 through 31 as named above.

The compounds of the present invention can be prepared by a combination of chemical and enzymatic methods. The monosaccharides, and the trisaccharides containing two beta-D-N-acetylglucosamine units, can be synthesized using chemical methods. To these, two galactose units can be added in one step enzymatically with UDP-galactose and galactosyl transferase to generate pentasaccharides. The pentasaccharides can be enzymatically disialylated to produce the bivalent heptasaccharides.

More specifically, 5-(methoxycarbonyl)pentyl β-D-galactopyranoside, (monosaccharide 1), can be prepared by reacting acetobromogalactose with 5-methoxycarbonylpentanol. Monosaccharide 1 is converted to the 4,6-O-benzylidene or 2,3-isopropylidene derivative by treatment with α,α-dimethoxytoluene or 2,2-dimethoxypropane, respectively, to provide 5-(methoxycarbonyl)pentyl 4,6-O-benzylidene-β-D-galactopyranoside (monosaccharide 3); or 5-(methoxycarbonyl)pentyl 3,4-isopropylidene-β-D-galactopyranoside (monosaccharide 5) respectively. 5-(methoxycarbonyl)pentyl 3-O-allyl-β-D-galactopyranoside (monosaccharide 2) can be prepared from monosaccharide 1 by selective allylation with di-n-butyltin oxide and allyl bromide. Selective blocking of the 6-hydroxyl group of monosaccharide 2 with t-butyldimethylsilyl chloride affords 5-methoxycarbonyl)pentyl 3-O-allyl-6-(t-butyl-dimethylsilyl)-β-D-galactopyranoside (monosaccharide 4).

Treatment of monosaccharide 3 or of monosaccharide 5 with allyl bromide and sodium hydride followed by removal of the benzylidene or the isopropylidene group with p-toluenesulfonic acid in methanol yields 5-(methoxycarbonyl)pentyl 2 3-di-O-allyl-β-D-galactopyranoside (monosaccharide 8) and 5-(methoxycarbonyl)pentyl 2,6-di-O-allyl-β-D-galactopyranoside (monosaccharide 6) respectively. Under the allylation conditions with sodium hydride and allyl bromide, a methyl ester attached as a tether group on the galactose can be partially converted to the allyl ester, which can not be easily separated by chromatography. However, treatment of the crude product with sodium methoxide in methanol converts the allyl ester to the methyl ester.

Finally 5-(methoxycarbonyl)pentyl 2,4-di-O-benzoyl-β-D-galactopyranoside (monosaccharide 7) can be obtained in two steps from monosaccharide 4 by converting monosaccharide 4 to the 2,4-di-O-benzoate followed by simultaneous removal of the allyl and t-butyldimethyl groups. To do this the 3-O-allyl group is isomerized to the isopropyl derivative with Ir(-COD)[($C_6H_5$)$CH_3P]_2PF_6$. Treatment of this with aqueous mercuric chloride removes both the isopropenyl and the t-butyldimethylsilyl groups.

With the exception of monosaccharide 7, all of the remaining monosaccharides discussed above have the least electron withdrawing alkyl or alkenyl groups in order to preserve the maximum reactivity of the remaining hydroxyl groups in the glycosylation reactions.

The trisaccharides of the present invention can be prepared by chemical synthesis from the monosaccharides. For example, monosaccharides 3 to 8 as defined above can be reacted with 2-deoxy-2-phthalimido-3,4,6-tri-O-acetyl-α-β-D-glucopyranosyl bromide in the presence of silver triflate and collidine to give the corresponding trisaccharides 9 to 15. These compounds are:

5-(methoxycarbonyl)pentyl 4,6-O-benzylidene-2,3-di-O-(2-deoxy-3,4,6-tri-O-acetyl-2-phthalimido-β-D-glucopyranosyl)-β-D-galactopyranoside (trisaccharide 9);

5-(methoxycarbonyl)pentyl 3-O-allyl-6-O-(t-butyldimethylsilyl)-2,4-di-O-(2-deoxy-3,4,6-tri-O-acetyl-2-phthalimido-β-D-glucopyranosyl)-β-D-galactopyranoside (trisaccharide 10);

5-(methoxycarbonyl)pentyl 2,6-di-O-(2-deoxy-3,4,6-tri-O-acetyl-2-phthalimido-β-D-glucopyranosyl)-3,4-O-isopropylidene-β-D-galactopyranoside (trisaccharide 11);

5-(methoxycarbonyl)pentyl 2,6-di-O-allyl-3,4-di-O-(2-deoxy-3,4,6-tri-O-acetyl-2-phthalimido-β-D-glucopyranosyl)-β-D-galactopyranoside (trisaccharide 12);

5-(methoxycarbonyl)pentyl 2,4-di-O-benzoyl-3,6-di-O-(2-deoxy-3,4,6-tri-O-acetyl-2-phthalimido-β-D-glucopyranosyl)-β-D-galactopyranoside (trisaccharide 13); and 5-(methoxycarbonyl)pentyl 2,3-di-O-allyl-4,6-di-O-(2-deoxy-3,4,6-tri-O-acetyl-2-phthalimido-β-D-glucopyranosyl)-β-D-galactopyranoside (trisaccharide 14).

The reaction is facile for monosaccharides such as 5 and 8 which each have a primary and a secondary hydroxyl groups. The choice of the protecting groups in the monosaccharide is important. Groups for the protection of oxygen suitable for use in the present invention are acetyl, hydrogen, benzal, benzoyl, trialkylsilyl, alkyl or alkenyl. Groups for the protection of O-protected glucosamine are acetyl or acyl. Groups for the protection of nitrogen suitable for use in the present invention are acetyl and phthalimido. The choice of protecting group is dictated by synthetic convenience, and is well known by those skilled in the art. The protecting group 3-O-allyl-6-t-butyldimethylsilyl is preferred for use herein. Even though the introduction of 2-deoxy-2-phthalimdo-3,4,6-tri-O-acetyl group causes severe steric crowding at the adjacent positions, still the vicinally substututed 2,3-trans-trisaccharide (trisaccharide 9) and also the cis-trisaccharide (trisaccharide 13) can be made.

Even though the monosaccharides such as 3, 4 and 6 react slowly and incompletely, only three equivalents of the bromide are recommended for use. The protected trisaccharide products comigrate with the bromide hydrolyzed product, namely 2-deoxy-2-phthalimido-3,4,6-tri-O-acetyl α,β-D-glucopyranose, (a rising from excess bromide) on silica gel columns under various solvent composition conditions making their purification difficult. In these cases the impurity can be removed in subsequent steps by converting the protected trisaccharides to more polar products.

The removal of the protecting groups in trisaccharides 9 through 14 yields the completely deprotected trisaccharides 15 through 20 as follows:

5-(methoxycarbonyl)pentyl 2,3-di-O-(2-acetamido-2-deoxy-β-D-glucopyranosyl)-β-D-galactopyranoside (trisaccharide 15);

5-(methoxycarbonyl)pentyl 2,4-di-O-(2-acetamido-2-deoxy-β-D-glucopyranosyl)-β-D-galactopyranoside (trisaccharide 16);

5-(methoxycarbonyl)pentyl 2,6-di-O-(2-acetamido-2-deoxy-β-D-glucopyranosyl)-β-D-galactopyranoside (trisaccharide 17);

5-(methoxycarbonyl)pentyl 3,4-di-O-(2-acetamido-2-deoxy-β-D-glucopyranosyl)-β-D-galactopyranoside (trisaccharide 18);

5-(methoxycarbonyl)pentyl 3,6-di-O-(2-acetamido-2-deoxy-β-D-glucopyranosyl)-β-D-galactopyranoside (trisaccharide 19); and 5-(methoxycarbonyl)pentyl 4,6-di-O-(2-acetamido-2-deoxy-β-D-glucopyranosyl)-β-D-galactopyranoside (trisaccharide 20).

The deprotection can be achieved using procedures commonly known in the art. For example, the di-O-benzylidene and isopropylidene groups in trisaccharides such as 9 and 11 can be removed by refluxing in methanol containing p-toluenesulfonic acid, whereas the phthalimido groups are removed with hydrazine in refluxing methanol. The irridium catalyst can be used for the isomerization of the O-allyl groups in trisaccharides such as 10, 12 and 14 to the corresponding 2-propenyl derivative which hydrolyzes upon treatment with aqueous mercuric chloride. The mercuric chloride treatment also removes the t-butyl-dimethyl group (as in trisaccharide 13) as well. Since each of the trisaccharides produce two equivalents of phthalhydrazide as an insoluble byproduct, for the purpose of convenient purification, following removal of O- and N-protecting groups, the product can be peracetylated to enable purification by silica gel chromatography. The acetate groups can be removed easily with sodium methoxide in methanol except in the case of a 3,4-substituted trisaccharide (see Example 18), where the acetate group attached to the 2-positionn of the reducing galactose can be removed by heating with sodium methoxide solution at 60° C. for 48 hours.

The trisaccharides of the present invention can then be converted enzymatically to the pentasaccharides and heptasaccharides of the present invention. Trisaccharides containing two β-N-acetyl-glucosamine groups can be treated with slightly more than two equivalents of UDP-galactose and bovine galactosyl transferase. This elaborates two lactosamine sequences to yield pentasaccharides. The use of phosphate resin columns (pH 6.8, 200 to 400 mesh) instead of chloride columns is desirable to obtain high purity products. The enzymatic digalactosylation requires about 24 hours and typically no monogalactosylated material is generated. When treating trisaccharides 15 through 20 above according to this procedure the pentasaccharides 21 to 26 as follows are obtained:

5-(methoxycarbonyl)pentyl 2,3-di-O-{β-D-galactopyranosyl-(1→4)-2-acetamido-2-deoxy-β-D-glucopyranosyl}-β-D-galactopyranoside (pentasaccharide 21);

5-(methoxycarbonyl)pentyl 2,4-di-O-{β-D-galactopyranosyl-(1→4)-2-acetamido-2-deoxy-β-D-glucopyranosyl}-β-D-galactopyranoside (pentasaccharide 22);

5-(methoxycarbonyl)pentyl 2,6-di-O-{β-D-galactopyranosyl-(1→4)-2-acetamido-2-deoxy-β-D-glucopyranosyl}-β-D-galactopyranoside (pentasaccharide 23);

5-(methoxycarbonyl)pentyl 3,4-di-O-{β-D-galactopyranosyl-(1→4)-2-acetamido-2-deoxy-β-D-glucopyranosyl}-β-D-galactopyranoside (pentasaccharide 24);

5-(methxyocarbonyl)pentyl 3,6-di-O-{β-D-galactopyranosyl(1→4)-2-acetamido-2-deoxy-β-D-glucopyranosyl}-β-D-galactopyranoside (pentasaccharide 25); and 5-(methoxycarbonyl)pentyl 4,6-di-O-{β-D-galactopyranosyl(1→4)-2-acetamido-2-deoxy-β-D-glucopyranosyl}-β-D-galactopyranoside (pentasaccharide 26).

The pentasaccharides of the present invention can be converted to heptasaccharides by the method of Sabesan and Paulson, J. Am. Chem. Soc., 108, 2068–2080 (1986). The pentasaccharides are treated with CMP-N-acetylneuraminic acid and galactose-β-1,4-N-acetylglucosamine-α-2,6-sialyl-transferase for about 24 hours. In addition to the disialylated heptasaccharides, small amounts of monosialylated product and sialic acid may be obtained. These can be conveniently removed by absorption of the total products on a phosphate resin column. Elution with 5 mM phosphate buffer provides the monosialylated product followed by the free sialic acid (N-acetylneuraminic acid). Subsequent elution with 50 mM phosphate buffer provides highly pure disialylated material followed by elution of cytidine monophosphate. This enzymatic sialylation works well for the 2,4-, 2,6-, 3,6-, and 4,6-pentasaccharides but the 2,3-penta-saccharide reacts more slowly.

The preferred heptasaccharides of the present invention prepared from pentasaccharides 21 to 26 according to this process are as follows:

5-(methoxycarbonyl)pentyl 2,3-di-O-{5-acetamido-3,5-dideoxy-D-glycero-D-galacto-2-nanulopyranosylonic acid(2→6)-β-D-galactopyranosyl(1→4)-2-acetamido-2-deoxy-β -D-glucopyranosyl}-β-D-galactopyranoside (heptasaccharide 27);

5-(methoxycarbonyl)pentyl 2,4-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside (heptasaccharide 28);

5-(methoxycarbonyl)pentyl 2,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactpyranoside (heptasaccharide 29);

5-(methoxycarbonyl)pentyl 3,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside (heptasaccharide 30); and 5-(methoxycarbonyl)pentyl 4,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside (heptasaccharide 31).

The structural identity and complete proton and carbon chemical shifts assignments of the trisaccharides, pentasaccharides and heptasacchardies of the invention can be achieved by nuclear magnetic resonance spectroscopy.

The heptasaccharides can be evaluated as inhibitors of the influenza virus hemagglutination of the resialylated human erythrocytes. This can be done according to the procedue of Pritchett et al., *J. Biol. Chem.*, 264, 9850-9859 (1989), which is herein incorporated by reference. Weakly binding methyl-α-D-acetylneuraminic acid can be used as a reference compound. It shows 50% inhibition at 3.50 mM concentration. Heptasaccharides having the two trisaccharides anchored at the 3- and 6-positions of the galactose exhibit as high as 10 fold increased inhibitory potency as compared to monovalent sialosides. There is a general increase in binding potency going from heptasaccharides having the trisaccharides bound at the 2- and 3-positions to that having them bound at the 3- and 6-positions. The binding drops in heptasaccharides having the trisaccharides bound at the 2- and 6-positions. Heptasaccharides having the trisaccharides bound at the 2- and 4-positions have about the same inhibitory potency as monovalent sialoside. Bovine serum albumin glycosylated with a 3,6-heptasaccharide shows even greater inhibitory potency suggesting the therapeutic potential of a macromolecule containing this heptasaccharide for influenza viral inhibition.

Thus the heptasaccharides of the present invention are useful as viral inhibitors for the inhibition of influenza virus of human isolates. The pentasaccharides of the present invention are useful as intermediates in the preparation of the heptasaccharides, and to inhibit galactose binding lectins. The trisaccharides of the present invention are useful as synthetic intermediates in the preparation of the pentasaccharides and heptasaccharides of the present invention, and to inhibit N-acetylglucosamine binding lectins. The monosaccharides of the present invention are useful as synthetic intermediates in the preparation of the trisaccharides used to prepare the pentasaccharides and heptasaccharides of the present invention.

The following examples illustrate the present invention, but are not intended to limit it in any manner.

In the following Examples, unless specified, all reagents were purchased from Aldrich Chemical Co. Thin layer chromatography was performed on precoated plates of Silica Gel 60 $F_{254}$ (EM Science), and the spots were visualized with a spray containing 5% sulfuric acid in ethanol followed by heating. Column chromatography was done on silica Gel 60 (230–400 mesh, EM Science). Elemental analysis was performed in Galbraith Laboratories, Inc., Knoxville, Tenn. Optical rotations were measured with a Perkin-Elmer 241 polarimeter at ambient temperatures. The structural identities were established by NMR methods. $^1$H NMR spectra were recorded at 300 or 500 or 600 MHz (GE NMR QE-300, QE 500 or Bruker AMX 600) and the $^{13}$C-NMR spectra were recorded at 75.48 or 125.16 MHz. The hydrogen and carbon chemical shifts (Table 1) in $CDCl_3$ are expressed relative to tetramethylsilane. For solutions of compounds in deuterium oxide or deuterated methanol, the hydrogen chemical shifts are expressed relative to HOD signal (4.80 ppm at 296° K.), and the carbon chemical shifts are expressed relative to external TMS using the deuterium lock of the spectrometer, which set the chemical shifts of 1,4-dioxane at 66.9 ppm.

EXAMPLE 1

5-(Methoxycarbonyl)pentyl β-D-galactopyranoside (1)

A solution cf acetobromogalactose (38.4 g) in 200 mL dry dichloromethane was added over a period of 60 min to a vigorously stirred suspension containing 5-methoxycarbonylpentanol (30.0 g), anhydrous silver carbonate 31.7 g, Aldrich), 3 Å molecular sieves (30.0 g) and anhydrous calcium sulphate (20.0 g) in dry dichloromethane (350 mL). After 20 h, the solution was filtered over celite and the solution was evaporated to dryness. The syrup was dissolved in pyridine (75 mL) containing acetic anhydride (50 mL) and 4-N,N-dimethylaminopyridine (10 mg) and stirred at room temperature for 3 h. The reaction mixture was then poured over crushed ice (200 g) and the product was extracted with dichloromethane (2×200 mL). The combined dichloromethane layer was washed with ice cold 1M hydrochloric acid and this procedure was repeated till the aqueous layer was acidic. Finally, the dichloromethane layer was washed with saturated sodium bicarbonate solution, dried over anhydrous magnesium sulphate and evaporated. To the crude syrup, n-hexane was added (200 mL), shaken well and the hexane layer was decanted. This procedure was repeated thrice. Finally, the syrup was dissolved in anhydrous methanol (300 mL). 15 mL of 0.5M sodium methoxide solution was added and this mixture was stirred at room temperature for 3 h. The reaction mixture was neutralized with IR-120 $H^+$ resin, filtered and evaporated to a dry residue to yield the titled compound (26.1 g). $[\alpha]_D^{25}$ −3.8±2° (c 1.03, MeOH). $^1$H n.m.r.($CD_3OD$) ∂: 4.19 (d, J=7.3 Hz, H-1), 3.89 and 3.54 (m, 2 H, $OCH_2$-of aglycon), 3.82 (dd, J=1.0, 3.2 Hz, H-4), 3.76–3.68 (m, H-6a,b), 3.64 (s, $COOCH_3$), 3.50–3.47 (m, H-2, H-5), 3.44 (dd, J=3.2, 9.5 Hz, H-3), 2.32 (t, J=7.3 Hz, $CH_2COO$), 1.65 and 1.40 (6 H, hydrogens of pentyl group). $^{13}$C n.m.r. ($CD_3OD$) ∂: 105.1, 76.8, 75.3, 72.8, 70.6, 70.6, 62.7, 52.0, 34.9, 30.5, 26.8, 25.9. Anal. Calcd for $C_{13}H_{24}O_8$: C, 50.6; H, 7.8. Found: C, 49.47; H, 7.78.

EXAMPLE 2

5-(Methoxycarbonyl)pentyl 3-O-allyl-β-D-galactopyranoside (2)

Compound 2 was prepared from 1 according to the literature procedure (J. Carbohydr. Chem. 8 (1989) 145) as follows. Compound 1 of Example 1 (20.0 g) was refluxed in anhydrous benzene (500 mL) containing 3 Å molecular sieves (20 g) for 1 h followed by the addition of di-n-butyltin oxide (24.0 g) and the refluxing was continued for 4 more h. To this tetraethylammonium bromide (7.0 g) and allyl bromide (80 mL) were added and refluxed for another 1 h followed by stirring at room temperature for 36 h. The reaction mixture was evaporated to dryness and the product was extracted with $CH_2Cl_2$, washed with 10% aqueous KF solution, ice cold 1M hydrochloric acid (HCl) and saturated sodium bicarbonate ($NaHCO_3$) solution. Chromatography of the crude product on a column of Silica gel using ethyl acetate-hexane-ethanol = 10:10:1 as eluant gave the titled compound 2 (16.2 g). $[\alpha]_D^{25}$ −3.5±2° (c 0.96, $CHCl_3$). $^1H$ n.m.r. ($CDCl_3$ +$D_2O$<5%) ∂: 5.97 (m, —CH=C), 5.35, 5.30, 5.24 and 5.20 (m, $CH_2$=C), 4.23 (m, O—$CH_2$—C=, H-1, $J_{1,2}$=7.5 Hz), 4.05 (d, J=3.5 Hz, H-4), 3.96-3.80 and 3.50-3.40 (m, O—$CH_2$—C, H-6a,b, H-5), 3.72 (dd, J=7.5, 9.5 Hz, H-2), 3.36 (dd, J=3.5, 9.5 Hz, H-3), 2.32 (t, J=7.0 Hz, $CH_2COO$), 1.64 and 1.40 ((6 H, hydrogens of pentyl group). $^{13}C$ n.m.r.($CD_3OD$) ∂: 176.0, 136.7, 117.3, 105.1 (C-1), 82.6 (C-3), 76.6 (C-5), 71.94, 71.89, 70.6, 67.6 (C-4), 62.7 (C-6), 52.0, 34.9, 30.5, 26.8, 25.9. Anal. Calcd for $C_{16}H_{28}O_8 \cdot H_2O$: C, 52.46; H, 8.20. Found: 52.84; H, 7.93.

EXAMPLE 3

5-(Methoxycarbonyl)pentyl 4,6-O-benzylidene-β-D-galactopyranoside (3)

A solution of compound 1 of Example 1 (20.0 g) in dry acetonitrile (200 mL) containing α,α-dimetoxytoluene (12.0 mL) and p-toluenesulfonic acid (1.0 g) was stirred at room temperature for 3.5 h. The solution was neutralized with triethylamine (5 mL) and the solution was evaporated to dryness. The residue was dissolved in $CH_2Cl_2$ (300 mL) and washed with water, 0.5M ice cold HCl and saturated $NaHCO_3$ solution. The solution was dried over anhydrous magnesium sulfate, filtered and evaporated. The solid obtained was washed with diethylether to remove the impurities and this procedure provided the titled compound 3 as a colorless solid (21.6 g, 84% yield) homogeneous on tlc (ethyl acetate-hexane-ethanol=5:5:1). $[\alpha]_D^{25}$ −20.5±2° (c 1.08, MeOH). The structure of the product was Confirmed by $^1H$ n.m.r. ($CD_3OD$) ∂: 7.54 and 7.33 (m, 5 H, $C_6H_5$), 5.58 (s, 1 H, PhCH—), 4.28 (m due to virtual coupling, H-1), 4.19 (dd, H-6a), 4.17 (H-4), 4.12 (dd, H-6b), 3.89 and 3.55 (m, 2 H, O—$CH_2$-of the aglycon), 3.64 (s, $COOCH_3$), 3.60 (m, H-2, H-3), 3.51 (m, H-5), 2.33 (t, $CH_2COO$), 1.64 and 1.42 (6 H, hydrogens of pentyl group). $^{13}C$ n.m.r. ($CD_3OD$) ∂: 176.1, 139.9, 129.9, 129.1, 127.7, 104.9, 102.6, 77.7, 74.1, 72.3, 70.7, 70.5, 68.3, 52.0, 34.9, 30.5, 26.7, 25.9. Anal. Calcd for $C_{21}H_{27}O_8$: C, 61.76; H, 6.86. Found: C, 60.45; H, 7.07.

EXAMPLE 4

5-(Methoxycarbonyl)pentyl 3-O-allyl-6-(t-butyldimethylsilyl)-β-D-galactopyranoside (4)

Compound 2 of Example 2 (10.85 g) was dissolved in dry dimethylformamide (DMF, 120 mL) containing imidazole (1.63 g) and 4 Å molecular sieves and cooled in an ice bath. To this, t-butyldimethylsilyl chloride (tBDMS chloride, 3.6 g) was added and stirred at this temperature for 10 min and then at room temperature 1 h. Another portion of imidazole (1.05 g) and tBDMS chloride (2.34 g) were added to the ice cold solution and stirred for 1 h. Methanol (1 mL) was added and the reaction mixture was evaporated to dryness. The residue was dissolved in $CH_2Cl_2$ and washed with water, 1M ice cold HCl and saturated $NaHCO_3$ solution. The solution was dried over anhydrous magnesium sulfate, filtered and evaporated. $^1H$ n.m.r. of the crude product (12.0 g of colorless solid) showed it to be essentially pure titled compound. $[\alpha]_D^{25}$ −3.2±2° (c 1.03, $CHCl_3$). $^1H$ n.m.r.($CDCl_3$ +$D_2O$<5%) ∂: 5.95 (m, 1 H, —CH=C), 5.33 and 5.23 (m, 2 H, C=$CH_2$), 4.24 (m, 3 H, H-1, $J_{1,2}$=Hz, O—$CH_2$—C=), 4.06 (d, H-4), 3.9-3.8 (m, 3 H, H-6a,b, $OCH_2$—C), 3.73 (dd, H-2), 3.67 (s, $COOCH_3$), 3.52 (m, $OCH_2$—C), 3.44 (m, H-5), 3.35 (dd, H-3), 2.32 (t, $CH_2COO$), 1.65 and 1.40 (6 H, hydrogens of pentyl group), 0.89 (s, t-butyl group), 0.09 (d, $CH_3$—Si—$CH_3$). $^{13}C$ n.m.r. ($CDCl_3$) ∂: 173.9, 134.8, 117.4, 103.2, 80.7, 75.0, 71.2, 71.0, 69.3, 66.3, 62.2, 51.3, 33.9, 29.2, 25.9, 25.6, 24.6, 18.3, −5.34, −5.39. Anal. Calcd for $C_{22}H_{42}O_8Si$: C, 57.14; H, 9.09. Found: C, 56.30; H 9.06.

EXAMPLE 5

5-(Methoxycarbonyl)pentyl 3,4-isopropylidene-β-D-galactopyranoside (5)

Compound 1 of Example 1 (16.0 g), 2,2-dimethoxypropane (660 mL) and camphorsulfonic acid (660 mg) were stirred at room temperature for 48 h. The solution was neutralized with triethylamine and the solvent from the mixture was evaporated. The residue was co-evaporated with toluene twice and the residue was dissolved in 10:1 methanol-water mixture (600 mL) and refluxed for 5 h under nitrogen atmosphere. The solvent was evaporated and the residue was coevaporated with toluene to remove traces of water. The product 5 was obtained in pure form after chromatography on a column of silica gel using ethyl acetate-hexane-water = 10:10:1 as eluant. Weight of the recovered product was 13.0 g. $[\alpha]_D^{25}$ +18.1±2° (c 1.05, $CHCl_3$). $^1H$ n.m.r. ($CDCl_3$) ∂: 4.18 (d, J=7.8, H-1), 4.12 (dd, H-4), 4.10 (dd, H-3), 4.0 3.6 (m, 3 H, H-6a,b, H-5, $OCH_2$—C), 3.68 (s, $COOCH_3$), 3.54 (m, 2 H, H-2 and $OCH_2$—C), 2.33 (t, —$CH_2COO$), 1.8-1.3 (m,12 H, hydrogens of pentyl group and isopropylidene methyl groups). $^{13}C$ n.m.r. ($CD_3OD$) ∂: 176.1, 111.1, 104.2, 81.2, 75.3, 75.2, 74.7, 70.6, 62.8, 52.0, 34.9, 30.5, 28.5, 26.7, 26.6, 25.9. Anal. Calcd for $C_{16}H_{28}O_8$: C, 55.17; H, 8.05. Found: C, 55.02; H, 7.98.

EXAMPLE 6

5-(Methoxycarbonyl)pentyl 2,6-di-O-allyl-β-D-galactopyranoside (6)

Compound 5 of Example 5 (2.4 g) was dissolved in DMF (20 mL) containing 4 Å sieves, cooled in ice bath and 50% sodium hydride suspension in paraffin (864 mg) was added. After 10 min, allyl bromide (1.85 mL) was added and the solution was stirred at room temperature for 24 h. The reaction mixture Was neutralized with methanol (3 mL) and the solution was poured in to a separatory funnel containing $CH_2Cl_2$ (50 mL) and ice cold 1M aqueous HCl. The organic layer was separated and washed with 1M ice cold HCl and saturated $NaHCO_3$ solution. The solution was dried over anhydrous magnesium sulfate, filtered and evaporated. This crude product was employed in the next step. An analytical sample was prepared by purification of the portion of the crude product on a column of silica gel using ethyl acetate-hexane = 1:5. $[\alpha]_D^{25}$ +10.7±2° (c 1.05, $CHCl_3$). $^1H$ n.m.r. ($CDCl_3$) ∂: 5.90 (m, 2 H, 2x —CH=C), 5.30, 5.25, 5.20-5.10 (m, 4 H, 2x C=$CH_2$), 4.33-4.18 (m, 3 H, $OCH_2$C=, H-1, $J_{1,2}$=8.2 Hz), 4.15-3.98 (m, 4 H, H-4, H-3, $OCH_2$C=), 3.94-3.82 (m, 2 H, H-5, O—$CH_2$C), 3.64 (s, COOCH$_3$), 3.46 (m, O—CH$_2$C), 3.29 (dd, J$_{2,3}$=6.6 Hz), 2.29 (t, CH$_2$COO), 1.65 and 1.40 (6 H, hydrogens of pentyl group), 1.49 and 1.32 (isopropylidene methyl groups). $^{13}$C n.m.r.(CDCl$_3$) δ: 173.8, 135.2, 134.8, 116.6, 109.8, 103.0, 79.9, 79.2, 74 0, 72.6, 72.6, 72.4, 69.5, 51.2, 34.0, 29.4, 27.9, 26.3. 25.7, 24.8. Anal. Calcd for C$_{22}$H$_{36}$O$_8$: C, 61.68; H, 8.41. Found: C, 61.46; H, 8.37.

The above residue was dissolved in anhydrous methanol (100 mL) containing p-toluenesulfonic acid monohydrate (135 mg) and refluxed for 60 min. The solution was neutralized with triethylamine, evaporated to dryness. Chromatography of the crude product on a column of Silica gel using ethyl acetate-hexane-ethanol =100:100:7.5 as eluant gave the titled compound 6 (1.63 g). [α]$_D^{25}$ −6.7±2° (c 1.08, CHCl$_3$). $^1$H n.m.r.(CDCl$_3$) δ: 5.89 (m, 1 H, —CH=C), 5.29, 5.24, 5.17 and 5.14 (m, 2 H, CH$_2$=C—), 4.38 and 4.15 (m, 2 H, O—CH$_2$CH=), 4.35 (d, J=7.6 Hz, H-1), 4.0 (m, 2 H, H-4 and H-6a), 3.90 and 3.47 (m, 2 H, O—CH$_2$—C), 3.64 (s, COOCH$_3$), 3.77-3.50 (m, H-6b, H-5 and H-3), 3.38 (dd, J=7.6, 8.5 Hz, H-2), 2.33 (t, CH$_2$COO), 1.65 and 1.43 (6 H, hydrogens of pentyl group). $^{13}$C n.m.r. (CDCl$_3$) δ: 173.8, 135.1, 134.5, 117.0, 103.8, 79.2, 73.50, 73.45, 72.6, 69.6, 69.4, 69.2, 51.3, 34.0, 29.4, 25.8, 24.8. Anal. Calcd for C$_{19}$H$_{32}$O$_8$: C, 58.76; H, 8.25. Found: C, 58.32; H, 8.30.

EXAMPLE 7

5-(Methoxycarbonyl)pentyl 2,4-di-O-benzoyl-β-D-galactopyranoside (7)

Crude compound 4 of Example 4 (12.0 g) was dissolved in CH$_2$Cl$_2$ (200 mL) containing anhydrous pyridine (20.9 mL). To this, benzoyl chloride (12 mL) and 4-N,N-dimethylaminopyridine (100 mg) were added and the solution was stirred at room temperature for 16 h. The reaction mixture was poured over ice and diluted with CH$_2$Cl$_2$ (200 mL). The CH$_2$Cl$_2$ layer was separated and washed with 1M ice cold HCl and saturated NaHCO$_3$ solution. The solution was dried over anhydrous magnesium sulfate, filtered and evaporated. Chromatography of the crude product on a column of Silica gel using ethyl acetate-hexane=1:6 as eluant gave 5-(methoxycarbonyl)pentyl 3-O-allyl-2,4-di-O-benzoyl-6-(t-butyldimethylsilyl)-β-D-galactopyranoside (16.3 g) [α]$_D^{25}$ +57.3±2° (c 1.03, CHCl$_3$). $^1$H n.m.r. (CDCl$_3$) δ: 8.12, 8.04, 7.55 and 7.45 (m, 10 H, 2 x C$_6$H$_5$), 5.80 (d, J=3.2 Hz, H-4), 5.67 (m, 1 H, —CH=C), 5.43 (dd, J=8.1, 10.0 Hz, H-2), 5.16 and 5.13 (m, 2 H, CH$_2$=C), 4.60 (d, J=8.1 Hz, H-1), 4.16 and 3.99 (m, 2 H, —OCH$_2$C=), 3.95–3.83 (m, 5 H, H-6a,b, H-3, H-5, one of O—CH$_2$ of aglycon), 3.61 (s, COOCH$_3$), 3.48 (m, O—CH$_2$ of aglycon), 2.10–1.95 (m, CH$_2$COO), 1.58, 1.45 and 1.20 (6 H, hydrogens of pentyl group), 0.89 (s, C$_4$H$_9$—Si), −0.02, −0.03 (2 x CH$_3$Si). $^{13}$C n.m.r. (CDCl$_3$) δ: 173.8, 165.6, 165.1, 134.4, 132.9, 132.8, 130.5, 130.2, 130.11, 130.07, 129.95, 129.6, 129.4, 128.6, 128.4, 128.3, 117.1, 101.8, 77.4, 74.6, 72.0, 70.7, 69.5, 67.1, 61.5, 51.2, 33.8, 29.2, 25.8, 25.5, 24.6, 18.2, −5.5. Anal. Calcd for C$_{36}$H$_{50}$O$_{10}$Si; C, 64.4S; H, 7.46. Found: C, 63.69; H, 7.48.

5-(Methoxycarbonyl)pentyl 3-O-allyl-2,4-di-O-benzoyl-6-(t-butyldimethylsilyl)-β-D-galactopyranoside (7.8 g) was dissolved in freshly distilled dry tetrahydrofuran (THF, 200 mL) and gently evacuated and equilibrated under nitrogen atmosphere. 1,4-Dicyclooctadienyl bis(-diphenylmethylphosphine)irridium (I) hexafluorophosphate (200 mg) was added and the equilibration under nitrogen atmosphere was continued twice. The solution was then exposed to hydrogen atmosphere and maintained till the color of the reaction became light yellow. At this time, the reaction mixture was gently evacuated and equilibrated with nitrogen. The solution was stirred under this for 48 h and evaporated to dryness. The residue was dissolved in 10% mercuric chloride solution in 90% aqueous acetone (170 mL) and stirred for 30 min. The solution was evaporated to dryness and the residue was dissolved in dichloromethane (150 mL) and washed with water, 10% potassium iodide solution, 1M ice cold HCl and saturated NaHCO$_3$ solution. The solution was dried over anhydrous magnesium sulfate, filtered and evaporated. Chromatography of the crude product on a column of Silica gel using ethyl acetate-hexane=1:1 as eluant gave the titled compound 7 (4.50 g). [α]$_D^{25}$ +59.0±2° (c 1.03, CHCl$_3$). $^1$H n.m.r. (CDCl$_3$) δ: 8.15, 8.08, 7.62 and 7.50 (m, benzoate hydrogens), 5.54 (broad d, J=3.4 Hz, H-4), 5.38 (dd, J=7.8, 10.0 Hz, H-2), 4.67 (d, J=7.8 Hz, H-1), 4.10 (dd, J=3.4, 10.0 Hz). 3.85 (broad t, J=6.4 Hz, H-5), 3.76 (dd, J=6.6, 12.0 Hz, H-6b), 3.94 and 3.56 (m, O—CH$_2$—C), 3.62 (s, COOCH$_3$), 3.56 (m, H-3), 2.10 (m, —CH$_2$CO), 1.56 and 1.26 ((6 H, hydrogens of pentyl group). $^{13}$C n.m.r. (CDCl$_3$) δ: 173.8, 167.4, 166.8, 133.7, 133.3, 133.2, 130.13, 130.06, 129.8, 129.7, 129.1, 128.6, 128.4, 128.3, 101.4, 74.2, 74.1, 71.9, 71.4, 69.9, 60.8, 51.2, 33 8, 29.2, 25.5, 24.5. Anal. Calcd for C$_{27}$H$_{32}$O$_{10}$: C, 62.79; H, 6.20. Found: C, 62.43; H, 6.24.

EXAMPLE 8

5-(Methoxycarbonyl)pentyl 2,3-di-O-allyl-β-D-galactopyranoside (8)

Compound 3 of Example 3 (11.7 g) was dissolved in DMF (180 mL) containing 4 Å sieves, cooled and sodium hydride (2.4 g) was added. After 10 min, allyl bromide (14 mL) was added and the solution was stirred at room temperature for 16 h. The reaction mixture was quenched with methanol (5 mL) and the solution was evaporated to dryness. The residue was dissolved in dichloromethane and washed with water, 1M ice cold HCl and saturated NaHCO$_3$ solution. The solution was dried over anhydrous magnesium sulfate, filtered and evaporated. Examination of the product by $^1$H n.m.r. showed that in addition to the titled compound 8, (5-methoxycarbonylpentyl 4,6-O-benzylidene-2,3-di-O-allyl-β-D-galactopyranoside), a significant amount of 5-allyloxycarbonylpentyl 4,6-O-benzylidene-2,3-di-O-allyl-β-D-galactopyranoside was also formed. However, the allyl ester could be easily converted to the titled compound 8 as described below. An analytical sample was prepared by chromatography on a column of silica gel using ethyl acetate-hexane=3:8. M.p. 75.6° C. [α]$_D^{25}$ +20.7±2° (c 1.02, CHCl$_3$). $^1$H n.m.r.(CDCl$_3$) δ: 7.51 and 7.34 (m, 5 H, hydrogens of the phenyl group), 5.93 (m, 2 H, 2 x —CH=C), 5.59 (s, benzalic hydrogen), 5.34, 5.30, 5.27, 5.24, 5.16, 5.14, 5.10, 5.08 (m, 4 H, 2 x CH$_2$=C), 4.37 (d, J=7.6 Hz, H-1), 4.33 (dd, J=1.0, 3.6 Hz, H-4), 4.34–4.14 (m, 6 H, 2x O—CH$_2$—C=, H-5, H-6a), 4.12 (dd, J=1.7, 12.5 Hz, H-6b), 3.93 and 3.54 (m, 2 H, O—CH$_2$—C), 3.65 (s, COOCH$_3$), 3.53 (dd, J=3.7, 9.8 Hz, H-3), 3.49 (dd, J=7.6, 9.8 Hz, H-2), 3.33 (broad s, H-5), 2.33 (t, J=7.3 Hz, CH$_2$COO), 1.64 and 1.45 (6 H, hydrogens of pentyl group). Anal. Calcd for C$_{26}$H$_{36}$O$_8$: C, 65.55; H, 7.56. Found: C, 65.62, H, 7.39.

In order to convert the allyl ester to the methyl ester, the above crude product was dissolved in methanol (200 mL) and to this 0.5M sodium methoxide solution (10 mL) as added and stirred at room temperature for 16 h. Examination by tlc (ethyl acetate-hexane=2:3) indicated one product. The solution was neutralized with H+ resin, filtered and evaporated. The product was purified by chromatography on a column of Silica gel using ethyl acetate-hexane (3:8) as eluant to colorless solid (8.3 g).

The above residue (8.0 g) was dissolved in anhydrous methanol (250 mL) containing p-toluenesulfonic acid (800 mg) and refluxed for 45 min. The solution was cooled, neutralized with triethylamine, and evaporated to dryness. The residue was dissolved in $CH_2Cl_2$ (250 mL) and washed with water, 1M ice cold HCl and saturated $NaHCO_3$ solution. The solution was dried over anhydrous magnesium sulfate, filtered and evaporated. Chromatography of the crude product on a column of Silica gel using ethyl acetate-hexane-ethanol=10:10:1 as eluant gave titled compound 8 (5.50 g). $[\alpha]_D^{25}$ −6.5 ±2° (c 1.13, $CHCl_3$). $^1$H n.m.r. (MeOH) ∂: 5.90 (m, 2 H, —C$\underline{H}$=C), 5.32, 5.28, 5.26, 5.23, 5.20, 5.16 and 5.12 (m, 4 H, 2x $CH_2$=C), 4.27 (d, J=Hz, H-1), 4.30 and 4.18 (m, 2x —C$\underline{H_2}$—C=), 3.64 (s, $COOCH_3$), 2.30 (t, $CH_2COO$), 1.63 and 1.41 (6 H, hydrogens of pentyl group). $^{13}$C n.m.r. ($CDCl_3$) ∂: 174.1, 135.1, 134.5, 117.4, 116.7, 103.6, 80.1, 78.3, 73.9, 73.8, 71.6, 69.7, 67.6, 62.5, 51.5, 33.9, 29.3, 25.6, 24.6. Anal. Calcd for $C_{19}H_{32}O_8$: C, 58.76; H, 8.25. Found: C, 57.65; H, 8.47.

EXAMPLE 9

5-(Methoxycarbonyl)pentyl 4,6-O-benzylidene-2,3-di-O-(2-deoxy-3,4,6-tri-O-acetyl-2-phthalimido-β-D-glucopyranosyl)-β-D-galactopyranoside (9)

Compound 3 of Example 3 (700 mg) was dissolved in dry nitromethane (15 mL) containing 4 Å molecular sieves (5.0 g), silver trifluromethanesulfonate (957 mg) and s-collidine (0.45 mL) and stirred under nitrogen at −25° C. A solution of 2-deoxy-2-phthalimido-3,4,6-tri-O-acetyl-α,β-D-glucopyranosyl bromide (1.85 g) in dichloromethane (5 mL) was added in drops. After 10 min, the reaction mixture was gradually warmed up to room temperature and left stirring for 3 h. Additional silver tirflate (686 mg), collidine (322 uL) and the bromide (1.29 g in 5 mL of $CH_3NO_2$) were added and the reaction was continued for another 16 h. It was then diluted with $CH_2Cl_2$ and filtered over a pad of Celite. The filtrate was washed with water, 5% sodium phiosulfate, 1M ice cold HCl and saturated $NaHCO_3$ solution. The solution was dried over anhydrous magnesium sulfate, filtered and evaporated. Chromatography of the crude product on a column of Silica gel using ethylacetate:hexane:ethanol 20:20:1 as eluant gave titled compound 9 (1.7 g, this was contaminated to about 10% with 2-deoxy-2-phthalimido-3,4,6-tri-O-acetyl-α,β-D-glucopyranose, which had near identical mobility as 9). $^1$H n.m.r.($CDCl_3$) ∂: 7.88–7.58 (m, phthalimido hydrogens), 5.74 and 5.66 (2x t, 2 H, J=10.5 Hz, H-3' and H-3"), 5.72 and 5.63 (2x d, J=8.0 Hz, 2 H, H-1' and H-1"), 5.37 (s, 1 H, benzalic hydrogen), 5.12 (broad t, 2 H, J=10 Hz, H-4' and H-4"), 3.65 (s, $COOCH_3$), 2.26 (t, —$CH_2COO$), 2.12, 2.08, 2.03, 2.02, 1.85 and 1.83 (6 s, $CH_3CO$), 1.54, 1.45 and 1.25 (6 H, hydrogens of pentyl group). $^{13}$C n.m.r. ($CDCl_3$) ∂: 175.6, 170.6, 170.5, 170.1, 169.9, 169.52, 169.49, 167.5, 137.7, 134.1, 133.9, 131.4, 131.2, 128.4, 127.8, 125.8, 123.6, 100.4, 100.1, 96.9, 95.9, 76.4, 75.5, 75.1, 71.9, 71.6, 71 2, 70.7, 69.0, 68.7, 68.2, 66.4, 62.5, 61.8, 55.0, 54.6, 51.4, 33.9, 29.1, 25.4, 24.7, 20.8, 20.7, 20.4. Anal. Calcd for $C_{60}H_{66}O_{26}N_2$: C, 58.54; H, 5.77; N, 2.28. Found: C, 58.04; H, 5.38; N, 2.15.

EXAMPLE 10

5-(Methoxycarbonyl)pentyl 3-O-allyl-6-O-(t-butyldimethylsilyl)-2,4-di-O-(2-deoxy-3,4,6-tri-O-acetyl-2-phthalimido-β-D-glucopyranosyl)-β-D-galactopyranoside (10)

Compound 4 of Example 4 (3.18 g) was dissolved in dry nitromethane (70 mL) containing 4 Å molecular sieves (15.0 g), silver trifluromethanesulfonate (3.30 g) and s-collidine (1.50 mL) and stirred under nitrogen at −25° C. A solution of 2-deoxy-2-phthalimido-3,4,6-tri-O-acetyl-α,β-glucopyranosyl bromide (6.37 g) in $CH_3NO_2$ (30 mL) was added in drops. After 10 min, the reaction mixture was gradually warmed up to room temperature and left stirring for 24 h. Additional silver tirflate (0.516 g), collidine (260 uL) and the bromide (1.0 g) were added and the reaction was continued for another 3 h. The reaction mixture was processed as described in Example 9. Chromatography of the crude product on a column of Silica gel (ethyl acetate-hexane=2:3 at the start to 3:2 at the end gave titled compound 10 as the protected trisaccharides 10 (3.45 g). Two disaccharide fractions (1.75 and 1.1 g, as evidenced by $^1$H n.m.r.) were also obtained. No attempt was made to convert these disaccharide fractions to the trisaccharide 10. M.p. 87.5° C. $[\alpha]_D^{25}$ −8.6±2° (c 1.04, $CHCl_3$). $^1$H n.m.r. ($CDCl_3$) ∂: 8.05–7.69 (m, phthalimido hydrogens, 5.75 and 5.71 (2 x t, J=10.3 Hz, H-3' and H-3"), 5.45 (m, — C$\underline{H}$=C, H-1', $J_{1',2'}$=8.5 Hz), 5.09 and 5.07 (2 x t, J=10.2 and 9.7, H-4' & H-4"), 4.95 (d, J=8.0 Hz, H-1"), 4.86 and 4.78 (2 x broad d, 2 H, J=10.3 and 17.4 Hz, C=$CH_2$), 4.35 (dd, J=4.3 and 12.1 Hz), 3.88 (d, J=3.5 Hz, H-4), 3.70 (s, $COOCH_3$), 3.37 (dd, J=7.8, 9.4 Hz, H-2), 3.14 (t, J=6.7 Hz), 3.02 (dd, J=2.5, 9.5 Hz), 2.32 (t, 2 H, $CH_2COO$), 2.13, 2.05 (2 x), 2.03, 1.87 and 1.84 (6 x $CH_3C\overline{O}$), 1.59, 1.37 and 1.26 (6 H, hydrogens of pentyl group), 0.84 (t-butyl), 0.03 and 0.01 ($C\underline{H_3}$—Si—$C\underline{H_3}$). $^{13}$C n.m.r. ($CDCl_3$) ∂: 174.1, 170.9, 170.5, 170.1, 169.4 (2x), 134.5, 134.2, 134.1, 123.6, 117.8, 101.3, 98.1, 97.3, 80.0, 76.4, 74.4, 72.1, 71.49, 71.46, 71.2, 70.4, 69.1, 67.8, 62.13, 62.10, 62.0, 54.9, 54.7, 34.0, 29.2, 25.8, 25.3, 20.8, 20.7, 20.6, 20.49, 20.46, −5.37, −5.42. Anal. Calcd for $C_{62}H_{80}O_{26}SiN_2$: C, 57.40; H, 6.17; N, 2.16. Found; C, 57.26; H, 6.14; N, 2.16.

EXAMPLE 11

5-(Methoxycarbonyl)pentyl 2,6-di-O-(2-deoxy-3,4,6-tri-O-acetyl-2-phthalimido-β-D-glucopyranosyl)-3,4-O-isopropylidene-β-D-galactopyranoside (11)

Compound 5 of Example 5 (700 mg) was dissolved in dry nitromethane (15 mL) containing 4 Å molecular sieves (5.0 g), silver trifluromethanesulfonate (957 mg) and s-collidine (0.45 mL) and stirred under nitrogen at −25° C. A solution of 2-deoxy-2-phthalimido-3,4,6-tri-O-acetyl-α,β-D-glucopyranosyl bromide (1.85 g) in dichloromethane (5 mL) was added in drops. After 10 min, the reaction mixture was gradually warmed up to room temperature and left stirring for 3 h. The reaction mixture was processed as described in Example 9. Chromatography of the crude product on a column of Silica gel (ethyl acetate-hexane=2:3) gave the protected trisaccharides titled compound 11 (1.56 g). M.p 121° C., $[\alpha]_D^{25}$ +31.3±2° (c 0.99, $CHCl_3$); $^1$H n.m.r. ($CDCl_3$) ∂:

7.83–7.69 ((m, phthalimido hydrogens), 5.80 and 5.76 (2x dd J=9.0, 10.8 Hz, H-3', H-3''), 5.40 (d, J=8.5 Hz, H-1''), 5.39 (d, J=8.4 Hz, H-1'), 5.16 (dd, J=9.0, 10.0 Hz, H-4'), 5.15 (dd, J=9.3, 10.3 Hz, H-4''), 4.36–4.25 (m, 4 H, H-6'a, H-6''b, H-2', H-2''), 4.14 (dd, J=2.2, 12.2 Hz, H-6'b), 4.07 (dd, J=2.0, 12.0 Hz, H-6''b), 4.02 (d, J=8.1 Hz, H-1), 3.90 (dd, J=3.4, 11.0 Hz, H-6a), 3.82 (m, 2 H, H-5', H-4), 3.70 (m, 6 H, COOC$\underline{H}_3$, H-6b, H-3, H-5''), 3.50 (m H-5), 3.42 and 3.25 (2x m, 2 H, O—CH$_2$—C), 3.27 (dd, J=6.6, 8.1 Hz, H-2), 2.31 (t, J=7.1 Hz, C$\underline{H}_2$COO), 2.080, 2.078, 2.012, 2.006, 1.84, 1.83 (6x s, C$\underline{H}_3$CO), 1.59, 1.37 and 1.20 (6 H, hydrogens of pentyl group), 1.00 and 0.7 (2x s, CH$_3$ of the isopropylidene group). $^{13}$C n.m.r. (CDCl$_3$) ∂: 174.0, 170.7, 170.6, 170.0, 169.49, 169.45, 134.3, 133.8, 131.3, 123.5, 123.3, 109.9, 100.8, 99.8, 97.8, 83.1, 78.2, 73.3, 71.8, 71.74, 71 69, 70.6, 70.4, 69.0, 68.8, 68.7, 68.5, 62.0, 61.8, 55.1, 54.5, 51.5, 33.9, 29.2, 27.2, 25.47, 25.43, 24.7, 20.7, 20.63, 20.60, 20.46, 20.41. Anal. Calcd for C$_{56}$H$_{66}$O$_{26}$N$_2$: C, 56.85; H, 5.58. Found: C, 55.05, H, 5.57.

EXAMPLE 12

5-(Methoxycarbonyl)pentyl 2,6-di-O-allyl-3,4-di-O-(2-deoxy-3,4,6-tri-O-acetyl-2-phthalimido-β-D-glucopyranosyl)-β-D-galactopyranoside (12)

Compound 6 of Example 6 (1.67 g) was dissolved in dry nitromethane (40 mL) containing 4 Å molecular sieves (5.0 g), silver trifluromethanesulfonate (3.43 g) and s-collidine (1.11 mL) and stirred under nitrogen at −25° C. A solution of 2-deoxy-2-phthalimido-3,4,6-tri-O-acetyl-α,β-D-glucopyranosyl bromide (6.64 g) in dichloromethane (10 mL) was added in drops. After 10 min, the reaction mixture was gradually warmed up to room temperature and left stirring for 16 h. The reaction mixture was processed as described in Example 9. Chromatography of the crude product on a column of Silica gel (ethyl acetate-hexane=3:2) gave a tlc homogeneous compound. Based on n.m.r. the product was identified as the protected trisaccharides titled compound 11 (1.51 g) along with 10% contamination by 2-deoxy-3,4,6-tri-O-acetyl-2-phthalimido-D-glucopyranose (as this has identical tlc mobility as 11). $^1$H n.m.r.(CDCl$_3$) ∂: 7.80–7.70 (m, phthalimido hydrogens), 5.942 (t, J=10.7 Hz, H-3'), 5.936 (d, J=8.5 Hz, H-1'), 5.86 (m, 1H, —CH=C), 5.62 (t, J=10.3 Hz, H-3''), 5.61 (d, J=8.8 Hz, H-1''), 5.32 (t, J=9.3 Hz, H-4'), 5.24 and 5.15 (m, 3 H, CH$_2$=C, H-4''), 4.66 (m, 1 H, —CH=C), 4.56 (dd, J=4.9, 12.2 Hz, H-6'a), 4.38 (dd, J=8.6, 10.5 Hz, H-2'), 4.32 (m, 1 H, one of CH$_2$=C), 4.29 dd, J=8.5, 10.7 Hz, H-2''), 4.26 (dd, J=4.2, 12.2 Hz, H-6''a), 4.21 (d, J=2.2 Hz, H-4), 3.99 (d, J=7.6 Hz, H-1), 3.74 (s, COOC$\underline{H}_3$), 3.39 (b t, H-5), 3.30 (dd, J=2.7, 10.0 Hz, H-3), 2.75 (dd, J=7.6, 10.0 Hz, H-2), 2.22 (t, J=7.6 Hz, CH$_2$COO), 2.19, 2.08, 2.05, 2.03, 1.89, 1.87 (6 x s, CH$_3$C$\overline{O}$O), 1.53, 1.43 and 1.23 (6 H, hydrogens of pentyl group). $^{13}$C n.m.r. (CD$_3$OD) ∂: 176.0, 172.4, 172.3, 171.8, 171.6, 171.4, 171.2, 169.8, 168.9, 168.6, 168.55, 135.6, 135.3, 135.2, 133.1, 132.7, 130.0, 124.3, 124.2, 104.7, 102.5, 99.1, 86.3, 75.7, 75.5, 73.3, 72.54, 72.51, 71.9, 70.9, 70.4, 70.3, 69.58, 69.56, 63.6, 63.0, 62.6, 55.9, 55.8, 52.0, 36.6, 30.1, 26.4, 25.7, 21.2, 20.68, 20.66, 20.61, 20.4, 20.3. Anal. Calcd for C$_{53}$H$_{62}$O$_{26}$N$_2$: C, 55.69; H, 5.43; N, 2.45. Found: C, 55.14; H, 5.44; N, 2.28.

To further characterize compound 11 and for elemental analysis, the allyl groups of compound 11 were removed and the resultant product (5-(Methoxycarbonyl)pentyl 3,4-di-O-(2-deoxy-3,4,6-tri-O-acetyl-2-phthalimido-β-D-glucopyranosyl)-β-D-galactopyranoside) could be separated from the 2-deoxy-3,4,6-tri-O-acetyl-2-phthalimido-D-glucopyranose impurity. This product was found to be pure by n.m.r. and suitable for optical rotation and elemental analysis. [α]$_D^{25}$ +36.6±2° (c 1.04, MeOH). $^1$H n.m.r. (CD$_3$OD) ∂: 7.71–7.80 (m, phthalimido hydrogens), 5.96 (d, J=8.6 Hz, H-1'), 5.94 (dd, J=9.3, 10.7 Hz, H-3'), 5.68 (dd, J=9.3, 10.5 Hz, H-3''), 5.58 (d, J=8.6 Hz, H-1''), 5.33 (dd, J=9.3, 10.0 Hz, H-4''), 5.06 (dd, J=9.0, 10.3 Hz, H-4'), 4.68 (dd, J=4.2, 12.5 Hz, H-6'a), 4.29–4.19 (m, 5 H, H-6'b, H-2', H-2'', H-6''a, H-4), 4.13 (dd, J=1.7, 12.2 Hz, H-6''b), 4.00 (m, 2 H, H-5' and H-5''), 3.94 (d, J=7.8 Hz, H-1), 3.71–3.62 (m, 3 H, H-6a,b, one of O—CH$_2$ of aglycon), 3.60 (s, COOC$\underline{H}_3$), 3.42 (dd, J=6.35, 7.33 Hz, H-5), 3.37 (dd, J=3.2, 10.0 Hz, H-3), 3.31 (m, one of O—CH$_2$ of aglycon), 2.87 (dd, J=7.8, 10.0 Hz, H-2), 2.23 (t, J=7.6 Hz, CH$_2$COO), 2.21, 2.08, 2.05, 2.03, 1.88, 1.80 (6 x s, CH$_3$C$\overline{O}$O), 1.50, 1.43 and 1.23 (6 H, hydrogens of pentyl group).

EXAMPLE 13

5-(Methoxycarbonyl)pentyl 2,4-di-O-benzoyl-3,6-di-O-(2-deoxy-3,4,6-tri-O-acetyl-2-phthalimido-β-D-glucopyranosyl)-β-D-galactopyranoside (13)

Compound 7 of Example 7 (1.50 g) was dissolved in dry nitromethane (80 mL) containing 4 Å molecular sieves (3.5 g), silver trifluromethanesulfonate (1.57 g) and s-collidine (0.7 mL) and stirred under nitrogen at −25° C. A solution of 2-deoxy-2-phthalimido-3,4,6-tri-O-acetyl-α,β-D-glucopyranosyl bromide (3.0 g) in nitromethane (20 mL) was added in drops. After 10 min, the reaction mixture was gradually warmed up to room temperature and left stirring for 16 h. Another portion of silver triflate (0.39 g) and collidine (0.2 mL) and a solution of the bromide (0.75 g) in nitromethane (20 mL) were added to the cooled (−28° C.) reaction mixture. After the addition, the reaction mixture was spontaneously warmed up to room temperature and stirred for 3 h. The reaction mixture was processed as described in Example 9. Chromatography of the crude product on a column of Silica gel (ethyl acetate-hexane-acetonitrile=3:6:2) gave the protected trisaccharides titled compound 13 (1.60 g). M.p. 119.6°–123.1° C. [α]$_D^{25}$ +50.9±2° (c 1.00, CHCl$_3$) $^1$H n.m.r. (CDCl$_3$) ∂: 8.01, 7.78, 7.68, 7.60, 7.44 & 7.42 (m, phthalimido and benzoate hydrogens), 5.74 and 5.55 (2 x dd, J=9.0, 10.8 Hz, H-3', H-3''), 5.55 (t, J=3.5 Hz, H-4), 5.48 (d, J=8.5 Hz, H-1'), 5.36 (d, J=8.3 Hz, H-1''), 5.29 (dd, J=8.1, 10.0 Hz, H-2), 5.15 (dd, J=9.3, 10.3 Hz, H-4'), 5.01) dd, J=9.3, 10.0 Hz, H-4''), 4.33 (dd, J=4.9, 12.5 Hz, H-6'a), 4.30 (m, H-1, H-2', J$_{1,2}$=8.1, J$_{1'2'}$=8.3, J$_{2'3'}$=10.5 Hz), 4.17 (dd, H-6'b), 4.14 (H-6''a), 4.10 (dd, J=8.2, 10.7 Hz, H-2''), 3.97 (dd, J=3.7, 10.0 Hz, H-3), 3.84 (m, H-5'), 3.80 (broad d, H-6a), 3.72 & 2.99 (m, 2 H, O—CH$_2$ of aglycon), 3.59 (s, COOC$\underline{H}_3$), 3.54 (dd, J=8.3, 11.0 Hz, H-6b), 3.28 (m, 1 H), 2.11, 2.02, 1.96, 1.95, 1.83, 1.69 (6 x s, CH$_3$COO). $^{13}$C n.m.r. (CDCl$_3$) ∂: 173.8, 169.9, 169.7, 169.3, 169.0, 167.4, 165.8, 164.5, 134.1, 133.6, 133.0, 132.6, 131.6, 131.0, 130.2, 129.8, 129.7, 129.4, 128.4, 128.1, 123.5, 123.1, 101.1, 98.5, 98.1, 78.1, 74.0, 72.1, 72.0, 71.5, 71.0, 70.7, 70.6, 69.4, 69.0, 68.9, 62.1, 61.7, 54.9, 54.6, 51.2, 33.7, 28.9, 25.3, 24.4, 20.61, 20.55, 20.51, 20.4, 20.3, 20.1. Anal. Calcd for C$_{67}$H$_{70}$O$_{28}$N$_2$: C, 59.55; H, 5.18; N, 2.07. Found: C, 59.03; H, 5.19; N, 2.06.

EXAMPLE 14

5-(Methoxycarbonyl)pentyl 2,3-di-O-allyl-4,6-di-O-(2-deoxy-3,4,6-tri-O-acetyl-2-phthalimido-$\beta$-D-glucopyranosyl)-$\beta$-D-galactopyranoside (14)

Compound 8 of Example 8 (7.50 g) was dissolved in dry nitromethane (250 mL) containing 4 Å molecular sieves (100 g), silver trifluromethanesulfonate (10.40 g) and s-collidine (4.7 mL) and stirred under nitrogen at $-25°$ C. A solution of 2-deoxy-2-phthalimido-3,4,6-tri-O-acetyl-$\alpha,\beta$-D-glucopyranosyl bromide (20.2 g) in dichloromethane (100 mL) was added in drops (1 h). After 1 h at $-28°$ C., additional silver triflate (2.86 g) and the bromide (5.5 g) in nitromethane (20 mL) were added and the reaction mixture was continued at this temperature for 2 more h. The reaction mixture was processed as described in Example 9. Chromatography of the crude product on a column of Silica gel (ethyl acetate-hexane-ethanol=20 20:1) gave the protected trisaccharides titled compound 14 (13.90 g). M.p. 108.6° C., $[\alpha]_D^{25}$ +23.4±2° (c 0.98, CHCl₃) ¹H n.m.r. (CDCl₃) $\partial$: 7.85–7.65 ((m, phthalimido hydrogens), 5.95 (dd, J=9.0, 10.7 Hz, H-3'), 5.81 (dd, J=9.0, 10.7 Hz, H-3''), 5.61 and 5.46 (m, 2 H, 2x CH=C), 5.39 (d, J=8.6 Hz, H-1''), 5.21 (d, J=8.6 Hz, H-1'), 5.19 (dd, J=9.0, 10.3 Hz, H-4''), 5.13 (dd, J=9.0, 10.0 Hz, H-4'), 5.06, 5.04, 5.01, 4.91, 4.90, 4.88 (m, 4 H, 2x CH₂=C), 4.48 (dd, J=2.4, 12.2 Hz), 4.36 (dd, J=3.66, 12.5 Hz), 4.22 (dd, J=2.0, 12.2 Hz), 4.05 (dd, J=3.7, 12.2 Hz (4 H, H-6'a,b, H-6''a,b), 4.30 (dd, J=8.3, 10.7 Hz, H-2'), 4.2 (dd, J=8.6, 10.7 Hz, H-2''), 3.93 (m, 1 H, H-5''), 3.90 (dd, J=2.7, 11.7 Hz, H-6a), 3.87 (d, J=7.8 Hz, H-1), 3.78 (m, 1 H, H-5'), 3.70 (H-6b), 3.67 (s, COOC$\overline{H}$₃), 3.54 (d, J=2.4 Hz, H-4), 3.27 (dd, J=2.0, 7.8 Hz, $\overline{H}$-5), 2.90 (dd, J=2.9, 9.8 Hz, H-3), 2.75 (dd, J=7.8, 9.8 Hz, H-2), 3.70, 3.47, 3.18 (m, 4 H, 2x —C$\underline{H}_2$—C=), 3.37 and 3.06 (m, 2 H, O—C$\underline{H}_2$— of pentyl group), 2.27 (t, J=7.6 Hz, 2 H, C$\underline{H}_2$COO), 2.17, 2.11, 2.03, 2.02, 1.87 and 1.84 (6x s, C$\overline{H}$₃CO), 1.56, 1.32 and 1.23 (6 H, hydrogens of pentyl group). ¹³C n.m.r. (CDCl₃) $\partial$: 174.0, 170.6, 170.5, 170.04, 170.02, 169.5, 169.4, 134.8, 134.6, 123.2, 117.7, 116.1, 102.7, 99.4, 97.7, 79.1, 78.6, 78.2, 73.5, 73.2, 72.3, 71.5, 71.1, 70.7, 70.1, 69.6, 68.9, 68.8, 69.7, 61.7, 61.0, 54.6, 54.3, 51.4, 33.9, 29.0, 25.5, 24.6, 20.8, 20.7, 20.6, 20.5, 20.4. Anal. Calcd for C₅₉H₇₀O₂₆N₂: C, 57.93; H, 5.73. Found: C, 57.30; H, 5.83.

EXAMPLE 15

5-(Methoxycarbonyl)pentyl 2,3-di-O-(2-acetamido-2-deoxy-$\beta$-D-glucopyranosyl)-$\beta$-D-galactopyranoside (15)

A solution of compound 9 of Example 9 (1.70 g) in anhydrous methanol (50 mL) containing sodium methoxide (100 umol) was stirred under dry nitrogen for 24 h, then neutralized with H+ resin, evaporated to a dry residue which was redissolved in anhydrous methanol (75 mL) containing hydrazine (375 uL) and refluxed for 8 h. The reaction mixture was evaporated to dryness and the residue was dissolved in pyridine (50 mL) and acetic anhydride (8 mL) containing DMAP (10 mg) and stirred for 16 h. The reaction mixture was poured over ice and diluted with CH₂Cl₂ (80 mL). The CH₂Cl₂ layer was separated and washed with 1M ice cold HCl and saturated NaHCO₃ solution. The solution was dried over anhydrous magnesium sulfate, filtered and evaporated. Chromatography of the crude product on a column of Silica gel using ethyl acetate-hexane-ethanol=5:5:1: as eluant gave the N-acetylated derivative of titled compound 9 (799 mg). This was dissolved in methanol (20 mL) containing p-toluenesulfonic acid (50 mg) and refluxed for 15 min. The solution was cooled, neutralized with triethylamine, and evaporated to dryness. The residue was dissolved in CH₂Cl₂ (75 mL) and washed with water, 1M ice cold HCl and saturated NaHCO₃ solution. The solution was dried over anhydrous magnesium sulfate, filtered and evaporated. The residue was redissolved in pyridine-acetic anydride (2:1, 15 mL). After 16 h, the product was worked up as described above and purified by high pressure liquid chromatography using ethyl acetate-hexane-ethanol=6:5:1 as eluant to get an amorphous product (645 mg). ¹H n.m.r.(CD₃OD) $\partial$: 5.43 (dd, J=9.5, 10.5 Hz, H-3'), 5.37 (dd, J=9.3, 10.5 Hz, H-3''), 5.35 (d, J=2.7 Hz, H-4), 5.13 and 5.02 (2 x d, J=8.3 Hz, H-1' and H-1''), 4.97 and 4.96 2 x t, J=10.0 Hz, H-4' and H-4''), 4.44 (d, J=7.6 Hz, H-1), 4.29 (dd, J=4.9, 12.5 Hz), 4.19 (d, 2H, J=3.2 Hz), 4.14–4.06 (m, 2 H), 3.98 (dd, J=7.6, 11.5 Hz), 3.66 (s, COOC$\overline{H}$₃), 3.54 (dd, J=8.3, 10.5 Hz, H-2'), 3.46 (dd, J=8.3, 10.3 Hz, H-2''), 2.36 (t, C$\overline{H}$₂COO), 2.06, 2.054, 2.046, 2.02, 2.00 (2x), 1.998 (2x), 1.994 and 1.989 (8 x s, 10 x C$\overline{H}$₃COO), 1.64 and 1.45 (6 H, hydrogens of pentyl group). ¹³C n.m.r. (CDCl₃) $\partial$: 174.3, 171.8, 171.4, 170.7, 170.53, 170.49, 170.45, 170.38, 169.59, 169.55, 102.4, 99.8, 99.6, 79.3, 77.6, 72.0, 71.9, 71.6, 71.5, 71 3, 69.7, 68.77, 68.75, 68.66, 63.0, 62.3, 61.1, 56.0, 55.3, 51.6, 33.8, 29.4, 25.7, 24.7, 23.7, 23.4, 20.73, 20.65, 20.5. The peracetylated derivative of titled compound 15 (645 mg) was deacetylated with methanol (20 mL) and sodium methoxide (125 umol) to get the trisaccharide titled compound 15 (330 mg) as a colorless powder. $[\alpha]_D^{25}$ −15.1±2° (c 1.0, H₂O). ¹H- and ¹³C- n.m.r. (D₂O) $\partial$: (see Tables 2 and 3, respectively). Anal. Calcd for C₂₉H₅₀O₁₈N₂: C, 48.74; H, 7.0; N, 3.9. Found: C, 46.04; H, 7.17; N, 4.23.

EXAMPLE 16

5-(Methoxycarbonyl)pentyl 2,4-di-O-(2-acetamido-2-deoxy-$\beta$-D-glucopyranosyl)$\beta$-D-galactopyranoside (16)

Compound 10 of Example 10 (3.1 g) was dissolved in freshly distilled dry tetrahydrofuran (THF, 120 mL) and gently evacuated and equilibrated under nitrogen atmosphere. 1,4-Dicyclooctadienyl-bis(diphenylmethylphosphine)irridium (I) hexaflurophosphate (120 mg) was added and the equilibration under nitrogen atmosphere was continued twice. The solution was then exposed to hydrogen atmosphere and maintained till the color of the reaction became light yellow. At this time, the reaction mixture was gently evacuated and equilibrated with nitrogen. The solution was stirred under this for 24 h and evaporated to dryness. The residue was dissolved in 10% mercuric chloride solution in 90% aqueous acetone (60 mL) and stirred for 30 min. The solution was evaporated to dryness. and the residue was dissolved in dichloromethane (150 mL) and washed with water, 10% potassium iodide solution, 1M ice cold HCl nd saturated NaHCO₃ solution. The solution was dried over anhydrous magnesium sulfate, filtered and evaporated. The residue was redissolved in pyridinea-cetic anydride (2:1, 15 mL) containing DMAP (10 mg). After 48 h, the product was worked up as described above. Chromatography of the crude product on a column of Silica gel using ethyl acetate-hexane=1:1 as eluant gave colorless solid (the allyl and the tert-butyldimethylsilyl group of compound 10 of Example 10 have been replaced with acetates, 2.58 g). $^1$H n.m.r. (CDCl$_3$) ∂: 8.03–7.73 (m, phthalimido hydrogens), 5.80 (dd, J=9.2, 10.7 Hz, H-3'), 5.54 (dd, J=9.1, 10.9 Hz, H-3''), 5.22 (d, J=8.1, H-1'), 5.13 (dd, J=9.2, 10.2 Hz, H-4'), 5.00 (dd, J=9.1, 10.2 Hz, H-4''), 4.69 (d, J=8.4, H-1''), 4.58 (dd, J=2.9, 10.2 Hz, H-3), 4.31 (dd, J=8.2, 10.7 Hz, H-2'), 4.21 (dd, J=2.9, 12.1 Hz,), 4.21 (d, J=7.3, H-1), 4.20 (dd, J=5.2, 12.1 Hz), 4.08 (dd, J=8.2, 10.7 Hz), 3.94 (broad d, J=3.0 Hz, H-4), 3.81 (dd, J=3.2, 12.1 Hz,), 3.74 (m, H-5'), 3.69 (s, —COOCH̄$_3$), 3.62 (m, 1 H, O—CH̄$_2$—C), 3.52 (broad t, J=6.3 Hz, H-5), 3.43 (dd, J=7.4, 10.3 Hz, H-2), 3.37 (m, 1 H, O—CH̄$_2$—C), 3.12 (m, H-5''), 2.34 (t, —CH̄$_2$COO), 2.15, 2.09, 2.03, 2.02, 2.00 (2x), 1.87, 1.80 (8 x CH̄$_3$CO), 1.61, 1.43 and 1.33 (6 H, aglyconic hydrogens).

A solution of the above residue n anhydrous methanol (50 mL) containing sodium methoxide (250 umol) was stirred under dry nitrogen for 16 h, then neutralized with H+ resin, evaporated to a dry residue which was redissolved in anhydrous methanol (125 mL) containing hydrazine (650 uL) and refluxed for 24 h. The reaction mixture was evaporated to dryness and the residue was suspended in methanol (50 mL) and acetic anhydride (2.5 mL). After 10 min, Et$_3$N (1 mL) and acetic anhydride (5 mL) were added and stirred at room temperature for 3 h. The solution was evaporated to dryness, redissolved in methanol (100 mL) containing H+ resin, stirred for 3 h and filtered. The filtrate was evaporated to dryness and redissolved in pyridine (50 mL) and acetic anhydride (15 mL) containing DMAP (10 mg). After 16 h, the product was worked up as described above. Chromatography of the crude product on a column of Silica gel using ethyl acetate-CH$_2$Cl$_2$-ethanol=10:10:1 as eluant gave a colorless solid (the peracetylated derivative of titled compound 16, 1.3 g). This was deacetylated with methanol (50 mL) and sodium methoxide (250 umol) to get the trisaccharide titled compound 16 (169 mg) as a colorless powder. $[\alpha]_D^{25}$ −15.9±2° (c 1.02, H$_2$O). $^1$H- and $^{13}$C-n.m.r.(D$_2$O) ∂: (see Tables 2 and 3, respectively). Anal. Calcd for C$_{29}$H$_{50}$O$_{18}$N$_2$: C, 48.74; H, 7.0; N, 3.9. Found: C, 44.19; H, 7.00; N, 3.82.

EXAMPLE 17

5-(Methoxycarbonyl)pentyl 2,6-di-O-(2-acetamido-2-deoxy-β-D-glucopyranosyl)-β-D-galactopyranoside (17)

To an ice cold solution of compound 11 of Example 11 (24.0 g) in CH$_2$Cl$_2$ (400 mL), 90% aqueous trifluoroactic acid (115 mL) was added and stirred. The progress of the reaction was monitored by tlc using ethyl acetate-hexane-ethanol=5:5:1 as eluant. After most of the starting material was consumed (about 45 min at ice bath temperature), the reaction mixture was washed twice with water and with saturated NaHCO$_3$ solution. Chromatography of the crude product on a column of Silica gel using ethyl acetate-hexane-ethanol=10:10:1 as eluant gave a colorless solid (the isopropylidene group of compound 11 of Example 11 has been removed, 17.8 g). M.p.; $[\alpha]_D^{25}$ $^1$H n m.r (CDCl$_3$) ∂: 7.82 and 7.73 (m, phthalimido hydrogens), 5.83 (t, J=10.3 hz, H-3'), 5.73 (t, J=9.9 Hz, H-3''), 5.54 (d, J=8.5 Hz, H-1'), 5.39 d, J=8.5 Hz, H-1''), 5.17 and 5.08 (2 x t, J=9.9 Hz, H-4' and H-4''), 4.12 (d, J=7.7 Hz, H-1), 3.68 (s, COOCH̄$_3$), 2.28 (t, —CH̄$_2$COO), 2.09, 2.07, 2.02 (2 x), 1.85 and 1.84 (6 x CH̄$_3$CO), 1.55, 1.34 and 1.23 (6 H, hydrogens of pentyl group). $^{13}$C n.m.r. (CDCl$_3$) ∂: 173.8, 170.4, 169.8, 169.28, 169.25, 167.9, 167.4, 134.3, 134.0, 131.8, 131.5, 123.5, 123.4, 101.3 (C-1), 98.6 and 98.2 (C-1' and C-1''), 80.5 (C-2), 72.7, 72.4, 72.2, 72.0, 70.9, 70.8, 69.3, 69.0, 68.3, 67.8, 62.2, 62.1, 55.0, 54.7, 51.3, 34.0, 29.3, 25.5, 24.7, 20.6, 20.49, 20.47, 20.31, 20.26.

A portion of the above residue (13.3 g) was dissolved in methanol (300 mL) containing sodium methoxide (2.5 mmol) and stirred at room temperature for 2 h (tlc, ethyl acetate-hexane-ethanol=5:5:1), neutralized with H+ resin, filtered and evaporated to a residue (10.3 g). $^1$H n.m.r. (D$_2$O) ∂: 7.91–7.78 (phthalimido hydrogens), 5.35 (d, J=8.5 Hz, H-1'), 5.22 (d, J=8.8 Hz, H-1''), 4.33 (dd, J=8.8, 10.6 Hz), 4.30 (dd, J=8.9, 10.7 Hz), 4.08 (d, 1 H, J=8.0 Hz, H-1), 3.69 (s, COOCH̄$_3$), 2.33 (t, CH̄$_2$COO), 1.47 and 1.13 (6 H, hydrogens of pentyl group).

The above residue in methanol (500 mL) containing hydrazine (2.2 mL) was refluxed for 16 h. It was then evaporated to a dry residue and coevaporated with pyridine to remove traces of hydrazine. The residue was dissolved in methanol (400 mL) followed by the addition of acetic anhydride (10 mL). After 20 min, acetic anhydride (20 mL) and Et$_3$N (4 mL) were added and the reaction mixture was stirred at room temperature for 24 h. A white precipitate (product) was obtained. This was filtered and the solid (residue 1) was washed with ethanol. The filtrate upon evaporation gave a solid (residue 2).

The residue 1 was dissolved in pyridine (100 mL) and evaporated and redissolved in anhdrous pyridine (100 mL) containing acetic anhydride (40 mL) and DMAP (200 mg) and stirred at room temperature for 5 h. The product was worked up as described above. Chromatography of the crude product on a column of Silica gel using ethyl acetate-CH$_2$Cl$_2$ -ethanol=10:10:1 as eluant gave colorless solid (10.0 g). $^1$H n.m.r.(CDCl$_3$) ∂: 5.81 and 5.62 (2 x broad s, NH̄—), 5.44–5.38 (m, 2 H, H-3' and H-3''), 5.30 (d, J=3.3 Hz, H-4), 5.07–4.99 (m, H-4', H-4'' and H-1'), 4.95 (dd, J=2.9, 9.9 Hz, H-3), 4.90 (d, J=8.5 Hz, H-1''), 4.42 (d, J=7.7 Hz, H-1), 4.29 (dd, J=4.0, 12.2 Hz), 4.24 (dd, J=4.5, 12.2 Hz), 4.10 (m), 3.68 (s, COOCH̄$_3$), 2.38 (t, CH̄$_2$COO), 2.11, 2.08, 2.07, 2.06, 2.02 (2 x), 2.01 (2 x), 1.96 AND 1.89 (10 x CH̄$_3$CO), 1.63 and 1.43 (hydrogens of pentyl group). This solid was dissolved in methanol (300 mL) containing sodium methoxide (2.5 mmol) and stirred for 24 h. A colorless solid was deposited in the reaction flask. The reaction mixture was cooled and the solid was filtered and washed with ice cold methanol. The residue was dissolved in water and lyophilized to get colorless solid of titled compound 17 (5.91 g). $[\alpha]_D^{25}$ −17.8±0.8 (c 1.09, H$_2$O). $^1$H- and $^{13}$C-n.m.r. (D$_2$O) ∂: (see Tables 2 and 3, respectively). Anal. Calcd for C$_{29}$H$_{50}$O$_{18}$N$_2$.H$_2$O: C, 47.54; H, 7.10. Found: C, 47.01, H, 7.12.

EXAMPLE 18

5-(Methoxycarbonyl)pentyl 3,4-di-O-(2-acetamido-2-deoxy-βD-glucopyranosyl)-β-D-galactopyranoside (18)

The ally protecting groups of compound 12 of Example 12 (0.94 g) were removed with irridium catalyst as described in Example 16 and the resultant product was acetylated with pyridine-acetic anhydride and purified by HPLC (ethyl acetate-hexane-ethanol=10:10:1) to get an amorphous material (290 mg, the isopropylidene group of compound 12 of Example 12 has been replaced with acetate groups). $^1$H n.m.r. (CDCl$_3$) ∂: 7.85–7.60 (m, phthalimido hydrogens), 5.90 (d, J=8.4 Hz, H-1″), 5.84 (dd, J=9.0, 10.7 Hz, H-3″), 5.61 (dd, J=9.3, 10.4 Hz, H-3′), 5.52 (d, J=8.5 Hz, H-1′), 5.28 (t, J=9.5 Hz, H-4′), 5.13 (dd, J=9.2, 9.8 Hz, H-4″), 4.53 (dd, J=5.2, 12.5 Hz), 4.48 (dd, J=8.0, 10.2 Hz, H-2), 4.33 (dd, J=8.5, 10.5 Hz, H-2′), 4.31 (broad d, exhibits nOe from H-1″, H-4), 3.90 (m, H-5′ and H-5″), 3.59 (s, COOCH$_3$), 3.50 (dd, J=2.7, 9.9 Hz, exhibits nOe from H-1′, H-3), 3.40 and 3.18 (m, O—CH$_2$C), 2.17 (m, CH$_2$COO, CH$_3$CO), 2.08, 2.01, 1.85, 1.83, (CH$_3$CO), 1.47, 1.30 and 1.10 (6 H, hydrogens of pentyl group). $^{13}$C n.m.r. (CDCl$_3$) ∂: 174.0, 170.7, 170.6, 170.4, 170.2, 169.9, 169.3, 167.7, 167.3, 134.1, 133.7, 131.5, 131.2, 123.8, 123.5, 123.3, 100.4, 99.9, 96.7, 81.4, 73.2, 72.1, 71.8, 71.2, 70.9, 70.6, 69.3, 68.7, 68.2, 67.3, 64.0, 62.0, 61.9, 54.4, 54.2, 51.3, 33.8, 28.9, 25.1, 24.5, 20.8, 20.7, 20.63, 20.57, 20.4, 20.3.

This was dissolved in methanol (20 mL) containing sodium methoxide (125 umol) and stirred at room temperature for 8 h (tlc, ethyl acetate-hexane-ethanol=5:5:1), neutralized with H$^+$ resin, filtered and evaporated to a residue (180 mg). This was dissolved in ethanol (15 mL) containing hydrazine (0.070 mL) was refluxed for 16 h. It was then evaporated to a dry residue and acetylated in pyridine-acetic anydride followed by purification by HPLC (Silica Gel, ethyl acetate-hexane-ethanol=5:5:1 eluant) to get the peracetylated derivative of 24 (180 mg). M. p. 110.3° C. [α]$_D^{25}$ −21.1±2° (c 1.03, MeOH).$^1$H n.m.r.(CDCl$_3$) ∂: 6.71 (d, J=8.5 Hz, NH), 6.27 (d, J=7.7 Hz, NH), 5.43 (dd, J=9.8, 10.4 Hz, H-3″), 5.35 (dd, J=9.8, 10.5 Hz, H-3′), 5.18 (d, J=8.5 Hz, H-1″), 5.10–4.96 (m, 4 H, H-4′, H-4″, H-2, H-1′), 4.68 (d, J=8.5 Hz, H-1), 4.16 (d, J=2.9 Hz, H-4), 3.63 (s, COOCH$_3$), 2.26 (t, —CH$_2$COO), 2.05, 2.04, 2.03, 2.00 (s, CH$_3$CO), 1.54 and 1.29 (6 H, hydrogens of pentyl group). $^{13}$C n.m.r. (CD$_3$OD) ∂: 174.2, 173.5, 172.4, 172.3, 172.0, 171.9, 171.8, 171.3, 171.25, 170.9, 104.2, 102.1, 101.6, 81.8, 75.9, 74.7, 73.4, 73.3, 73.1, 72.8, 71.3, 70.7, 70.5, 69.9, 65.2, 63.4, 63.3, 55.1, 54.9, 51.9, 34.8, 30.3, 26.6, 25.7, 23.0, 22.97, 21.1, 20.9, 20.8, 20.7, 20.6, 20.56. Anal. Calcd for C$_{45}$H$_{66}$O$_{26}$N$_2$: C, 51.43; H, 6.29. Found: C, 50.92; H, 6.30; N, 2.78.

This material (120 mg) was treated with sodium methoxide (0.125 mmol) in methanol (20 mL) at 60° C. for 48 h, cooled, neutralized with H$^+$ resin, filtered and evaporated to dryness. The residue was dissolved in 5 ml of deionized water and applied on a column of Bio Gel P2 (200–400 mesh). The fractions containing the titled compound 18 were pooled and lyophilized to get a colorless product (59 mg). [α]$_D^{25}$ ±° (c 1.03, water). $^1$H and $^{13}$C n.m.r. (see Tables 2 &3).

EXAMPLE 19

5-(Methoxycarbonyl)pentyl
3,6-di-O-(2-acetamido-2-deoxy-β-D-glucopyranosyl)-β-D-galactopyranoside (19)

Compound 13 (1.6 g) was dissolved in methanol (80 mL) containing sodium methoxide (0.5 mmol) and stirred at room temperature for 16 h (tlc, ethyl acetate-hexane-ethanol=10:10:1), neutralized with H$^+$ resin, filtered and evaporated to a residue (1.2 g). This residue in methanol (60 mL) containing hydrazine (0.27 mL) was refluxed for 24 h. It was then evaporated to a dry residue, which was redissolved in pyridine-acetic anhydride (4:1, 50 mL) containing DMAP (100 mg) and stirred for 16 h. This was then worked up as described above and the product was purified by HPLC using ethyl acetate-hexane-CH$_3$CN=2:1:2 to get two trisaccharide fractions (residue I=144 mg; residue II=380 mg,). Residue 1: [α]$_D^{25}$ +3.8±2° (c 1.00, MeOH) $^1$H n.m.r. of residue I (CDCl$_3$) ∂: 8.09, 8.01, 7.84, 7.73, 7.58 and 7.44 (m, benzoate hydrogens), 6.09 (broad s, NH), 5.65 (d, J=3.6 Hz, H-4), 5.52 (dd, J=8.1, 10.9 Hz, H-2), 5.36 and 5.35 (2x t, J=10.1 Hz, H-3′ & H-3″), 5.17 (d, J=8.0 Hz, NH), 5.07 (d, J=8.1 Hz, H-1′), 5.00 and 4.94 (2x t, J=9.6 Hz, H-4′ & H-4″), 4.75 (d, J=8.1 Hz, H-1″), 4.57 (d, J=8.0 Hz, H-1), 4.25 (dd, J=2.2, 12.4 Hz), 3.62 (s, COOCH$_3$), 2.04, 2.02, 2.01, 1.93, 1.90 (CH$_3$CO), 1.46, 1.24 and 1.17 ((6 H, hydrogens of pentyl group). $^{13}$C n.m.r. (CD$_3$OD) ∂: 173.2, 172.4, 172.3, 171.8 (2x), 171.7, 171.3, 171.2, 102.2, 102.0, 101.9, 78.6, 74.21, 74.16, 73.5, 73.0, 72.8, 72.1, 71.8, 70.4, 70.3, 70.2, 70.1, 63.3, 62.9, 56.3, 55.5, 52.0, 34.8, 30.2, 26.6, 25.7, 22.93, 22.90, 21.2, 20.8, 20.7, 20.6, 20.5. Anal. Calcd for C$_{45}$H$_{66}$O$_{26}$N$_2$: C, 51.43; H, 6.29. Found: C, 50.79; H, 6.32; N, 2.97.

Both residue I and II were the desired trisaccharides except that residue I had a benzoate group at the 2-position of the reducing galactose, while residue II was the peracetylated material. This was also confirmed when the residue I and II were deacylated with methanol (20 mL) and sodium methoxide (2.5 mmol for residue I, 24 h reaction time at room temperature and 5 mmol for residue II, 48 h reaction time at room temperature) and gave the trisaccharide 18 (240 mg of combined yield from residues I and II). $^1$H- and $^{13}$C-n.m.r.(D$_2$O) ∂: (see Table 2 & 3, respectively).

EXAMPLE 20

5-(Methoxycarbonyl)pentyl
4,6-di-O-(2-acetamido-2-deoxy-β-D-glucopyranosyl)-β-D-galactopyranoside (20)

Compound 14 of Example 14, (13.9 g) was dissolved in freshly distilled dry tetrahydrofuran (THF, 700 mL) and gently evacuated and equilibrated under nitrogen atmosphere. 1,4-Dicyclooctadienyl bis(diphenylmethylphosphine)irridium (I) hexaflurophosphate (638 mg) was added and the equilibration under nitrogen atmosphere was continued twice. The solution was then exposed to hydrogen atmosphere and maintained till the color of the reaction became light yellow. At this time, the reaction mixture was gently evacuated and equilibrated with nitrogen. The solution was stirred under this for 24 h and evaporated to dryness. The residue was dissolved in 10% mercuric chloride solution in 90% aqueous acetone (300 mL) and stirred for 30 min. The solution was evaporated to dryness and the residue was dissolved in CH$_2$Cl$_2$ and washed with water, 10% potassium iodide solution, 1M ice cold HCl and saturated NaHCO$_3$ solution. The solution was dried over anhydrous magnesium sulfate, filtered and evaporated. The residue was redissolved in pyridine-acetic anydride (4:1, 125 mL) containing DMAP (100 mg). After 24 h, the product was worked up as described above. Chromatography of the crude product on a column of Silica gel using ethyl acetate-hexane-ethanol=10:10:1 as eluant gave colorless solid (13.0 g). $^{13}$C n.m.r. (CDCl$_3$) ∂: 174.0, 170.9, 170.7, 170.55, 170.48, 170.09, 170.06, 169.5, 169.4, 168.1, 134.3, 134.0, 131.3, 123.6, 100.3, 98.0, 97.9, 74.7, 73.7, 72.5, 71.7, 71.6, 70.7, 70.0, 69.3, 68.83, 68.75, 68.4, 68.2, 61.7, 61.5, 54.6, 54.2, 51.4, 33.9, 28.9, 25.3, 24.6, 20.8, 20.6, 20.4, 20.3.

The above residue was dissolved in methanol (300 mL) containing sodium methoxide (2.5 mmol) and stirred at room temperature for 16 h (tlc, ethyl acetatehexane-ethanol = 10:10:1), neutralized with H+ resin, filtered and evaporated to a residue (9.2 g). This residue in methanol (700 mL) containing hydrazine (3.40 mL) was refluxed for 18 h. It was then evaporated to a dry residue, which was redissolved in pyridine (200 mL) and acetic anhydride (75 mL) containing DMAP (100 mg) and stirred for 16 h. Purification by chromatography on a column of Silica Gel using ethyl acetate-CH$_2$Cl$_2$ -ethanol = 5:5:1 gave an amorphous material (3.1 g). $[\alpha]_D^{25}$ −6.2±2° (c 1.03, MeOH). $^1$H n.m.r. (MeOH) ∂: 5.55 (dd, J=9.2, 9.8 Hz, H-3'), 5.16 (dd, J=9.2, 9.8 Hz, H-3''), 5.08 (dd, J=7.5, 9.8 Hz, H-2), 4.99 (dd, J=3.2, 9.8 Hz, H-3), 4.94 (t, J=9.2 Hz, H-4'), 4.90 (t, J=9.2 Hz, H-4''), 4.85 (d, J=8.1 Hz, H-1'), 4.63 (d, J=8.1 Hz, H-1''), 4.46 (d, J=8.0 Hz, H-1), 4.25 (m, 2 H, H-6 of GlcNAc), 4.17 (dd, J=4.5, 12.0 Hz, H-6 of GlcNAc), 4.13 (dd, J=2.4, 12.0, H-6 of GlcNAc), 4.03 (broad d, J=2.5 Hz, H-4), 3.93 (dd, J=3.4, 11.3 Hz, H-6a), 3.82 (dd, J=8.5, 10.7 Hz, H-2'), 3.69 (dd, J=8.0, 11.3 Hz, H-6b), 3.62 (s, COOCH$_3$), 2.28 (t, —CH$_2$—C), 2.06, 2.05, 2.03, 1.97, 1.95, 1.93, and 1.85 (s, CH$_3$CO), 1.58, 1.51 and 1.32 (6 H, hydrogens of pentyl group). $^{13}$C n m.r. (MeOH) ∂: 175.8, 173.8, 173.3, 172.31, 172.30, 172.0, 171.8, 171.2, 171.2, 102.4, 102.0, 101.2, 75.6, 74.5, 74.3, 74.2, 72.9, 72.8, 72.6, 71.0, 70.7, 70.2, 70.0, 63.2, 63.1, 56.7, 55.3, 52.0, 34.7, 30.2, 26.6, 25.7, 23.0, 22.9, 20.9, 20.8, 20.7, 20.63, 20.61, 20.57. Anal. Calcd for C$_{45}$H$_{66}$O$_{26}$N$_2$: C, 51.43; H, 6.29. Found: C, 50.64; H, 6.33. This amorphous material was dissolved in methanol (150 mL) containing sodium methoxide (1.5 mmol) and stirred at room temperature for 16 h. This was neutralized with H+ resin, filtered and evaporated to a residue which was redissolved in water and lyophilized. This was dissolved in 5 mL of deionized water and applied on a column of Bio Gel P2 (400 mesh) equilibrated and eluted with water. The UV active fractions at 220 nm (tlc, ethyl acetate-ethanol-water = 2:2:1) were pooled and lyophilized to get colorless solid titled compound 20 (1.02 g). $[\alpha]_D^{25}$ −24.1±2° (c 1.05, H$_2$O). $^1$H- and $^{13}$C-n.m.r. D$_2$O) ∂: (see Tables 2 and 3, respectively).

EXAMPLE 21

5-(Methoxycarbonyl)pentyl 2,3-di-O-{β-D-galactopyranosyl-(1→4)-2-acetamido-2-deoxy-β-D-glucopyranosyl}-β-D-galactopyranoside (21)

A solution of compound 15 of Example 15 (72 mg), uridinediphosphogalactose (UDP-galactose, 190 mg, Sigma Chemical Company, St. Louis, Mo., U.S.A.), bovine galactosyltransferase (EC 2:4.1.22, 6.2 U) and bovine serum albumin (3 mg) in 30 mM sodium cacodylate buffer (7 mL, pH 7.0) containing manganese chloride (40 umol) was incubated at 37° C. for 22 h. The reaction mixture was diluted to 20 mL with deionized water and applied on a column of AG ® 1-X2 (200–400 mesh, phosphate form, pH 6.8) and eluted with deionized water (100 mL). The solution was evaporated to dryness and the residue was dissolved in 5 mL of deionized water and applied on a column of Bio Gel P-2 (400 mesh) eluted and equilibrated with water. Fractions (7.5 mL) that showed UV absorption at 220 nm were examined by tlc using ethyl acetate-ethanol-water = 2:1:1 and were pooled and lyophilized to obtain colorless solid (74 mg). The structural identity of title compound 21 was unambiguously assigned by $^1$H- and $^{13}$C-n.m.r (see Tables 4 and 5, respectively).

EXAMPLE 22

5-(Methoxycarbonyl)pentyl 2,4-di-O-{β-D-galactopyranosyl-(1→4)-2-acetamido-2-deoxy-β-D-glucopyranosyl}-β-D-galactopyranoside (22)

A solution of compound 16 of Example 16 28 mg), UDP-galactose, (84 mg), bovine galactosyltransferase (5 U) and bovine serum albumin (3 mg) in 30 mM sodium cacodylate buffer (3 mL, pH 7.0) containing manganese chloride (40 umol) was incubated at 37° C. for 22 h. The reaction mixture was diluted to 20 mL and purified as described in Example 21. Yield of the product was 32 mg. The structural identity of titled compound 22 was unambiguously assigned by $^1$H- and $^{13}$C-n.m.r (see Tables 4 and 5, respectively).

EXAMPLE 23

5-(Methoxycarbonyl)pentyl 2,6-di-O-{β-D-galactopyranosyl-(1→4)-2-acetamido-2-deoxy-β-D-glucopyranosyl}-β-D-galactopyranoside (23)

A solution of compound 17 of Example 17 (72 mg), UDP-galactose, (190 mg), bovine galactosyltransferase (6 U) and bovine serum albumin (3 mg) in 30 mM sodium cacodylate buffer (7 mL, pH 7.0) containing manganese chloride (40 umol) was incubated at 37° C. for 22 h. The reaction mixture was diluted to 20 mL and purified as described in Example 21. Yield of the product was 95 mg. The structural identity of titled compound 23 was unambiguously assigned by $^1$H- and $^{13}$C-n.m.r (see Tables 4 and 5, respectively).

EXAMPLE 24

5-(Methoxycarbonyl)pentyl 3,4-di-O-{β-D-galactopyranosyl-(1→4)-2-acetamido-2-deoxy-β-D-glucopyranosyl}-β-D-galactopyranoside (24)

A solution of compound 18 of Example 18 (60 mg), UDP-galactose, (145 mg), bovine galactosyltransferase (6.25 U) and bovine serum albumin (3 mg) in 30 mM sodium cacodylate buffer (5.25 mL, pH 7.0) containing manganese chloride (40 umol) was incubated at 37° C. for 22 h. The reaction mixture was diluted to 20 mL and purified as described in Example 21. Yield of the product was 47 mg. The structural identity of titled compound 24 was unambiguously assigned by $^1$H- and $^{13}$C-n.m.r (see Tables 4 and 5, respectively).

EXAMPLE 25

5-(Methoxycarbonyl)pentyl 3,6-di-O-{β-D-galactopyranosyl(1→4)-2-acetamido-2-deoxy-β-D-glucopyranosyl}-β-D-galactopyranoside (25)

A solution of compound 19 of Example 19 (85 mg), UDP-galactose, (190 mg), bovine galactosyltransferase (6.25 U) and bovine serum albumin (3 mg) in 30 mM sodium cacodylate buffer (7 mL, pH 7.0) containing manganese chloride (40 umol) was incubated at 37° C. for 22 h. The reaction mixture was diluted to 20 mL and purified as described in Example 21. Yield of the product was 114 mg. The structural identity of titled compound 25 was unambiguously assigned by $^1$H- and $^{13}$C-n.m.r (see Tables 4 and 5, respectively).

EXAMPLE 26

5-(Methoxycarbonyl)pentyl
4,6-di-O-{β-D-galactopyranosyl(1→4)-2-acetamido-2-deoxy-β-D-glucopyranosyl}-β-D-galactopyranoside
(26)

A solution of compound 20 of Example 20 (72 mg), UDP-galactose, (190 mg), bovine galactosyltransferase (6.25 U) and bovine serum albumin (3 mg) in 30 mM sodium cacodylate buffer (7 mL, pH 7.0) containing manganese chloride (40 umol) was incubated at 37° C. for 22 h. The reaction mixture was diluted to 20 mL and purified as described in Example 21. Yield of the product was 98 mg. The structural identity of titled compound 26 was unambiguously assigned by $^1$H- and $^{13}$C-n.m.r (see Tables 4 and 5, respectively).

EXAMPLES 27–32

General Procedure For the Preparation and Purification of Sialosides

The pentasaccharide (Examples 21 to 26) and CMP-NeuAc were dissolved in 0.1M sodium cacodylate buffer (pH 6.5, 1 mL) containing Triton-CF 54 (0.1%) and bovine serum albumin (2 mg). The Galb1,4GlcNAc a2,6 sialyltransferase was added and the solution was incubated at 37° C. for 24 h. The reaction mixture was then diluted to 13 mL and applied on a column (1.5×9 cm) of Dowex 1-X2 (PO$_4$= form, 200–400 mesh). The column was washed with distilled water (175 mL) and then eluted with 5 mM sodium phosphate buffer (pH 6.8). Fractions (5 mL) were assayed for sialic acid by the periodate-resorcinol procedure of Jourdian, G. W., et al., *J. Biol. Chem.*, 246, 430–435 (1971) herein incorporated by reference. When no more sialic acid eluted out, the elution buffer was changed to 50 mM phosphate buffer (pH 6.8) when the desired disialoside started to elute out (as evidenced by periodateresorcinol procedure). These fractions containing the disialoside product, which eluted after free sialic acid, were pooled and evaporated to a dry residue. The product was then redissolved in 2 mL of water and applied on a column (1.6×24 cm) of Sephadex G-15 (Sigma) equilibrated and eluted with water. The fractions (1.5 mL) containing the sialyloligosaccharide, as evidenced by the periodate-resorcinol procedure, were measured for conductivity to exclude contamination by salts, pooled and lyophilized.

EXAMPLE 27

5-(Methoxycarbonyl)pentyl
2,3-di-O-{5-acetamido-3,5-dideoxy-D-glycero-D-galacto-2-nanulopyranosylonic
acid(2→6)-β-D-galactopyranosyl(1→4)-2-acetamido-2-deoxy-β-D-glucopyranosyl}-β-D-galactopyranoside
(27)

Compound 21 of Example 21 (16.0 mg), CMP-NeuAc (25 mg) and 2,6 sialyltransferase (296 mU) were incubated and the product isolated as described in the above general procedure to give 2.1 umol of the titled compound 27. For complete structural characterization by n.m.r. see Tables 6 and 7.

EXAMPLE 28

5-(Methoxycarbonyl)pentyl
2,4-di-O-{5-acetamido-3,5-dideoxy-D-glycero-D-galacto-2-nanulopyranosylonic
acid(2→6)-β-D-galactopyranosyl(1→4)-2--acetamido-2-deoxy-β-D-glucopyranosyl}-β-D-galactopyranoside (28)

Compound 22 of Example 22 (17.5 mg), CMP-NeuAc (37 mg) and 2,6 sialyltransferase (500 mU) were incubated, and the product isolated as described in the above general procedure to give 7.6 umol of the titled compound 28. From 5 mM phosphate eluted fractions, 2.1 umol of the monosialoside (28A) was obtained. For complete structural characterization by n.m.r. see Tables 6 and 7.

EXAMPLE 29

5-(Methoxycarbonyl)pentyl
2,6-di-O-{5-acetamido-3,5-dideoxy-D-glycero-D-galacto-2-nanulopyranosylonic
acid(2→6)-β-D-galactopyranosyl(1→4)-2-acetamido-2-deoxy-β-D-glucopyranosyl}-β-D-galactopyranoside
(29)

Compound 23 of Example 23 (17.0 mg), CMP-NeuAc (25 mg) and 2,6 sialyltransferase (296 mU) were incubated and the product isolated as described in the above general procedure to give 6.4 umol of the titled product 29. For complete structural characterization by n.m.r. see Tables 6 and 7.

EXAMPLE 30

5-(Methoxycarbonyl)pentyl
3,6-di-O-{5-acetamido-3,5-dideoxy-D-glycero-D-galacto-2-nanulopyranosylonic
acid(2→6)-β-galactopyranosyl(1→4)-2-acetamido-2-deoxy-β-D-glucopyranosyl}-β-D-galactopyranoside
(30)

Compound 25 of Example 25 (12.0 mg), CMP-NeuAc (37 mg) and 2,6 sialyltransferase (500 mU) were incubated and the product isolated as described in the above general procedure to give 14.4 mg of the titled compound 30. For complete structural characterization by n.m.r. see Tables 6 and 7.

EXAMPLE 31

5-(Methoxycarbonyl)pentyl
4,6-di-O-{5-acetamido-3,5-dideoxy-D-glycero-D-galacto-2-nanulopyranosylonic
acid(2→6)β-D-galactopyranosyl(1→4)-2-acetamido-2-deoxy-β-D-glucopyranosyl}-β-D-galactopyranoside
(31)

Compound 26 of Example 26 (12.0 mg), CMP-NeuAc (37 mg) and 2,6 sialyltransferase (500 mU) were incubated and the product isolated as described in the above general procedure to give 5.5μ mol of the titled compound. For complete structural characterization by n.m.r. see Tables 6 and 7.

EXAMPLE 32

5-[(2-benzyloxycarbonylaminoethyl)aminocarbonyl]-pentyl 3,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside (32)

A solution of compound 19 of Example 19 (440 mg) in methanol (20 mL) containing ethylenediamine (10 mL) was refluxed for 16 h, evaporated to a dry residue (509 mg) which was dissolved in a 2:1 water-dioxane mixture (15 mL) containing benzylchloroformate (585 mg). After 2 h, dioxane (5 mL) was added and the reaction mixture was stirred at room temperature for 16 h. The insoluble residue was filtered and the filtrate was evaporated to dryness, redissolved in water and passed through a column of mixed bed ion exchange resin (Dowex® MR-12, 50–100 mesh) equilibrated and eluted with water. The eluants were evaporated to dry a residue, dissolved in 5 ml of water and applied on a column of Bio gel P-2 (200–400 mesh) equilibrated and eluted with water. Fractions (76–80, 6 mL fractions) that had the product as evidenced by tlc (ethyl acetate-ethanol-water=2:2:1) were pooled and evaporated to a dry residue (68 mg).

A solution of the above residue (59 mg), UDP-galactose, (145 mg), bovine galactosyltransferase (6.25 U) and bovine serum albumin (3 mg) in 30 mM sodium cacodylate buffer (5.25 mL, pH 7.0) containing manganese chloride (30 umol) was incubated at 37° C. for 1 6 h. The reaction mixture was diluted to 20 mL and purified as described in Example 21. Yield of the product was 63 mg. The structural identity was unambiguously assigned by $^1$H n.m.r.

A portion of the above product (12.5 mg) in a buffer (pH 6.5, 2.0 mL) and CMP-NeuAc (37 mg), sodium cacodylate (200 umoles), triton (20 ug), bovine alkaline phosphatase (6 U) and 2,6 sialyltransferase (500 mU) were incubated for 30 h and the product isolated as described in the above general procedure to give 13 mg of the title compound 32.

EXAMPLE 33

Preparation of Bovine Serum Albumin (BSA)-compound 30 Conjugate (BSA-30 Conjugate)

A solution of compound 19 of Example 19 (75 mg) in methanol (10 mL) containing hydrazine (3 mL) was refluxed for 2.5 h, evaporated to a dry residue, redissolved in 5 mL of water and applied on a column of Bio Gel P2 (200–400 mesh) equilibrated and eluted with water. Fractions (8 ml) containing the product (fraction no. 59–69) were pooled and evaporated to a dry residue (75 mg).

The above product (10.4 mg, 10 u moles) in dry DMF (1 mL) was cooled to −30° C. A solution of hydrochloric acid (40 umoles) in DMF (100 uL) and t-butylnitrite (15 umoles) in DMF (100 uL) were added. After 60 min. at temperatures between −20° to −30° C., a solution of sulfamic acid (5 umoles) in DMF (100 uL) was added and the solution was maintained at −30° C. for 10 min. BSA (13 mg) in sodium borate-KHCO$_3$ buffer (pH 9.0, 5 mL) was cooled in an ice bath and the above DMF reaction mixture was added in drops. After gentle shaking at 4° C. for 16 h, the solution was diluted (to 10 mL) and dialyzed against deionized water for 3 days, replacing the the deionized water every 12 h. The solution was lyophilized and the residue was dissolved in a buffer (pH 6.5, 2 mL) containing sodium cacodylate (200 umoles), CMP-NeuAc (37 mg), triton (20 ug) and Galβ1,4GlcNAcα2,6 sialyltransferase (500 mU) and incubated for 24 h. The reaction mixture was then applied on a column of sephadex G-50 (fine) equilibrated and eluted with water and the fractions containing the product (UV absorption at 220 nm) were pooled and lyophilized to yield 7.2 mg of the BSA-30 conjugate.

TABLES

The numbers indicated in parenthesis in all tables correspond to the Example numbers.

TABLE 1

LIST OF OLIGOSACCHARIDES IN EXAMPLES 15 TO 31

TABLE 1-continued

LIST OF OLIGOSACCHARIDES IN EXAMPLES 15 TO 31

βDGal1,4βDGlcNAc1,4
　　　　　＼
　　　　　　βDGalOR¹  (26)
　　　　　／
βDGal1,4βDGlcNAc1,6

αDNeuAc2,6βDGal1,4βDGlcNAc1,2
　　　　　＼
　　　　　　βDGalOR¹  (27)
　　　　　／
αDNeuAc2,6βDGal1,4βDGlcNAc1,3

αDNeuAc2,6βDGal1,4βDGlcNAc1,2
　　　　　＼
　　　　　　βDGalOR¹  (28)
　　　　　／
αDNeuAc2,6βDGal1,4βDGlcNAc1,4

(28A)

LIST OF OLIGOSACCHARIDES IN EXAMPLES 15 TO 31

αDNeuAc2,6βDGal1,4βDGlcNAc1,2
　　　　　＼
　　　　　　βDGalOR¹  (29)
　　　　　／
αDNeuAc2,6βDGal1,4βDGlcNAc1,6

αDNeuAc2,6βDGal1,4βDGlcNAc1,3
　　　　　＼
　　　　　　βDGalOR¹  (30)
　　　　　／
αDNeuAc2,6βDGal1,4βDGlcNAc1,6

αDNeuAc2,6βDGal1,4βDGlcNAc1,4
　　　　　＼
　　　　　　βDGalOR¹  (31)
　　　　　／
αDNeuAc2,6βDGal1,4βDGlcNAc1,6

*R¹ = (CH₂)₅COOCH₃

TABLE 2

¹H chemical shifts of the trisaccharides
βDGlcNAc(1-x)[βDGlcNAc(1-y)]βDGal-O—(CH₂)₅COOCH₃ ∝

| Unit | | x = 2, y = 3 (15) | x = 2, y = 4 (16) | x = 2, y = 6 (17) | x = 3, y = 4 (18) | x = 3, y = 6 (19) | x = 4, y = 6 (20) |
|---|---|---|---|---|---|---|---|
| βBDGlcNAc 1-x | H-1 | 4.82 (8.5) | 4.79 (8.1) [0.99] | 4.50 (8.6) | 4.62 (8.6) | 4.69 (8.2) | 4.674 (8.3) |
| | H-2 | 3.53 (10.3) | 3.68 (10.3) | 3.70 (10.0) | 3.81 (10.3) | 3.74 (10.1) | 3.702 (10.0) |
| | H-3 | 3.68 (9.2) | 3.56 (9.0) [1.7?] | 3.54 (9.0) | 3.54 (8.5) | 3.56 (8.4) | 3.539 (9.0) |
| | H-4 | 3.45 (9.2) | 3.43 (9.1) | 3.42 | 3.48 | 3.46 | 3.450 (9.2) |
| | H-5 | 3.34 | 3.36 [1.03] | 3.42 | 4.44 | 3.43 | 3.388 |
| | H-6A | 3.91 (2.1, 12.2) | 3.88 (1.9) [0.59] | 3.90 (<2, 12.1) | 3.99 (2.0, 12.0) | 3.89 (1.4, 12.4) | 3.906 (<2, 11.9) |
| | H-6B | 3.77 (5.5) | 3.75 (5.5, 12.5) | 3.74 (5.0) | 3.77 (5.5) | 3.76 (5.1) | 3.755 (5.1) |
| | OCH₃ | 2.11ᵃ | 2.08ᵃ | — | — | 2.30ᵃ | |
| βBDGlcNAc 1-y | H-1 | 4.76 | 4.71 (8.3) [1.00] | 4.53 (8.4) | 4.93 (7.7) | 4.53 (8.3) | 4.514 (8.5) |
| | H-2 | 3.65 | 3.70 (10.3) | 3.69 (10.0) | 3.74 (10.7) | 3.70 (10.1) | 3.701 (10.0) |
| | H-3 | — | 3.57 (8.5) | 3.54 (9.0) | 3.55 (8.4) | 3.54 (8.2) | 3.536 (9.0) |
| | H-4 | 3.48 | 3.44 [1.5?] | 3.44 | 3.42 | 3.43 | 3.44 |
| | H-5 | 3.41 | 3.43 | 3.43 | 3.39 | 3.45 | 3.44 |
| | H-6A | 3.89 (<2,12.2) | 3.93 (<2) [0.63] | 3.93 (—, 12.2) | 3.90 (2.1, 12.0) | 3.93 (<2, 12.0) | 3.928 (<1, 12) |
| | H-6B | 3.76 (5.1) | 3.74 (5.2, 12.3) | 3.74 (4.6) | 3.73 (5) | 3.74 (4.8) | 3.751 (4) |
| | OCH₃ | 209ᵃ | 2.05ᵃ | — | — | 2.02ᵃ | |
| βBDGal 1-O | H-1 | 4.57 (8.2) | 4.48 (7.5) [0.96] | 4.43 (7.7) | 4.34 (7.5) | 4.31 (7.8) | 4.341 (8.0) |
| | H-2 | 3.80 (9.9) | 3.48 (9.2) [1.5] | 3.61 (9.9) | 3.36 (9.9) | 3.53 (9.8) | 3.351 (9.7) |
| | H-3 | 3.98 (3.1) | 3.81 (3.1) [1.13] | 3.67 (3.5) | 3.68 (2.4) | 3.68 (3.1) | 3.703 (2.9) |
| | H-4 | 4.13 | 4.03 [0.94] | 3.84 | 4.28 | 4.10 | 4.004 |
| | H-5 | — | 3.64 | — | — | — | 3.76 |
| | H-6A | — | 3.79 | — | — | — | 4.11 |
| | H-6B | — | 3.73 | — | — | — | 3.76 |
| (CH₂)₅COOCH₃ | H-1A | — | 3.85 [0.62] | — | — | — | |
| | H-1B | — | 3.65 [0.90] | — | — | — | |
| | H-2 | 1.64 | 1.62 [0.64] | — | — | 1.63 | |
| | H-3 | 1.40 | 1.39 [0.64] | — | — | 1.39 | |
| | H-4 | 1.64 | 1.63 [0.71] | — | — | 1.63 | |
| | H-5 | 2.42 | 2.42 [0.99] | — | — | 2.41 | |
| | OCH₃ | 3.69 | 3.69 [1.9] | 3.70 | — | 3.69 | 3.689 |

∝ The hydrogen chemical shifts are expressed relative to HOD (4.83 ppm, a acetone 2.23 ppm). The vicinal hydrogen-hydrogen coupling constants in hertzs and the proton spin-lattice relaxation times (T₁) in seconds are shown in the parenthesis and brackets, respectively.
ᵃ,ᵇ,ᶜThese assignments may be interchanged.
*overlapping signals affecting T₁ measurements.

βDGal1,4βDGlcNAc1,4
　　　　　＼
　　　　　　βDGal—OR¹
　　　　　／
αDNeuAc2,6βDGal1,4βDGlcNAc1,2

TABLE 3

¹³C Chemical shifts of the trisaccharides
βDGlcNAc(1-x)[βDGlcNAc(1-y)]βDGal-O)—(CH₂)₅COOCH₃ ∝

| Unit | | x = 2, y = 3 (15) | x = 2, y = 4 (16) | x = 2, y = 6 (17) | x = 3, y = 4 (18) | x = 3, y = 6 (19) | x = 4, y = 6 (20) |
|---|---|---|---|---|---|---|---|
| βDGlcNAc 1-x | C-1 | 99.6 (0.30) | 101.8 (0.33) | 102.2 (0.32) | 103.9 (0.37) | 103.4 (0.38) | 102.1 (0.38) |
| | C-2 | 57.8 (0.28) | 56.7 (0.32) | 56.7 (0.32) | 56.6 (0.35) | 56.4 (0.36) | 56.4 (0.36) |
| | C-3 | 73.8 (0.31) | 74.2 (0.35) | 74.5 (0.34) | 74.6 (0.37) | 74.4 (0.39) | 74.5 (0.37) |
| | C-4 | 70.6 (0.31) | 70.5 (0.32) | 70.6 (0.40) | 70.5 (0.37*) | 70.4 (0.34) | 0.5 (0.33) |
| | C-5 | 76.8 (0.29) | 76.6 (0.32*) | 76.6 (0.35) | 76.5 (0.35) | 76.4 (0.37) | 76.2 (0.37) |
| | C-6 | 61.2 (0.19) | 61.5 (0.20*) | 61.4 (0.21) | 61.4 (0.24) | 61.2 (0.21) | 61.5 (0.21) |
| | CON | 175.3 (1.2)ᵃ | 175.3 (1.8)ᵃ | 175.4 (1.7)ᵃ | 175.4 (2.1)ᵃ | 175.6 (—)ᵃ | 175.4 (—)ᵃ |
| | OCH₃ | 23.4 (0.92)ᵇ | 23.2 (1.2)ᵇ | 22.9 (1.3)ᵇ | 23.0 (1.2)ᵇ | 22.9 (1.3)ᵇ | 23.0 (1.1)ᵇ |
| βDGlcNAc 1-y | C-1 | 101.9 (0.30) | 102.4 (0.36) | 101.9 (0.38)ᶜ | 101.9 (0.30) | 102.1 (0.38) | 102.6 (0.36) |
| | C-2 | 57.1 (0.31) | 56.5 (0.34) | 56.1 (0.38) | 56.1 (0.33) | 56.2 (0.37) | 56.1 (0.39) |

TABLE 3-continued $^{13}$C Chemical shifts of the trisaccharides
βDGlcNAc(1-x)[βDGlcNAc(1-y)]βDGal-O—(CH$_2$)$_5$COOCH$_3$ ∝

| Unit | | x = 2, y = 3 (15) | x = 2, y = 4 (16) | x = 2, y = 6 (17) | x = 3, y = 4 (18) | x = 3, y = 6 (19) | x = 4, y = 6 (20) |
|---|---|---|---|---|---|---|---|
| | C-3 | 74.1 (0.34) | 74.4 (0.36) | 74.4 (0.39) | 74.6 (0.34*) | 74.5 (0.40) | 74.5 (0.39) |
| | C-4 | 70.4 (0.31) | 70.8 (0.34) | 70.5 (0.36) | 70.8 (0.33) | 70.6 (0.59) | 70.6 (0.37) |
| | C-5 | 76.6 (0.33) | 76.2 (0.33) | 76.5 (0.39) | 76.4 (0.35) | 76.5 (0.38) | 76.5 (—) |
| | C-6 | 61.1 (0.18) | 61.5 (0.20) | 61.6 (0.19) | 61.5 (0.23) | 61.4 (0.21) | 61.4 (0.22) |
| | CON | 175.2 (1.6)$^a$ | 175.1 (2.0)$^a$ | 175.0 (2.0)$^a$ | 175.3 (2.2)$^a$ | 175.0 (. . .)$^a$ | 174.9 (—)$^a$ |
| | OCH$_3$ | 23.2 (0.88)$^b$ | 23.0 (1.4)$^b$ | 22.9 (1.3)$^b$ | 23.0 (1.2)$^b$ | 23.0 (1.2)$^b$ | 22.9 (1.3)$^b$ |
| βDGal 1-O | C-1 | 101.4 (0.31) | 101.6 (0.30) | 102.0 (0.33)$^c$ | 103.4 (0.35) | 103.3 (0.33) | 103.2 (0.33) |
| | C-2 | 75.6 (0.26) | 78.9 (0.29) | 79.0 (0.30) | 70.5 (0.37*) | 70.4 (0.34) | 71.5 (0.33) |
| | C-3 | 81.4 (0.29) | 74.1 (0.30) | 73.3 (0.31) | 83.5 (0.28) | 82.7 (0.30) | 73.4 (0.31) |
| | C-4 | 69.4 (0.27) | 76.6 (0.32*) | 69.5 (0.28) | 75.8 (0.32) | 69.3 (0.30) | 77.2 (0.30) |
| | C-5 | 75.1 (0.30) | 74.6 (0.31) | 73.9 (0.31) | 74.6 (0.34*) | 74.0 (0.30) | 73.8 (0.32) |
| | C-6 | 61.4 (0.25) | 61.1 (0.22) | 69.3 (0.16) | 61.2 (0.24) | 70.0 (0.18) | 70.5 (0.25*) |
| (Ch$_2$)$_5$COOCH$_3$ | CH$_2$-1 | 70.6 (0.29) | 70.5 (0.29) | 70.8 (0.27) | 70.8 (0.38) | 70.7 (0.31) | 70.5 (0.25*) |
| | CH$_2$-2 | 29.2 (0.32) | 29.1 (0.35) | 29.1 (0.34) | 29.0 (0.44) | 29.0 (0.39) | 29.0 (0.41) |
| | CH$_2$-3 | 25.3 (0.33) | 25.2 (0.55) | 25.3 (0.50) | 25.2 (0.68) | 25.3 (0.58) | 25.3 (0.58) |
| | CH$_2$-4 | 24.7 (0.53) | 24.7 (0.73) | 24.7 (0.68) | 24.7 (0.68) | 24.7 (0.74) | 24.7 (0.84) |
| | CH$_2$-5 | 34.3 (0.71) | 34.3 (0.85) | 34.3 (0.79) | 34.4 (0.93) | 34.3 (0.93) | 34.2 (0.98) |
| | COO | 178.2 | 178.2 | 178.2 (. . .) | 179.7 | 178.3 (—) | 178.3 (—) |
| | OCH$_3$ | 52.7 (1.9) | 52.7 | 52.8 (2.4) | — | 52.8 (—) | 52.8 (2.6) |

∝ The carbon chemical shifts are expressed relative to 1,3-dioxane, using the deuterium lock of the spectrometer, which set the chemical shift of dioxane at 66.9 ppm. The spin-lattice relaxation times (T$_1$) in second are given in the parenthesis
$a,b,c$These assignments may be interchanged.
*Could not be determined precisely due to signal overlap.

TABLE 4

$^1$H Chemical shifts of the pentasccharides
βDGal(1-4)βDGlcNAc(1-x)[βDGal(1-4)βDGlcNAc(1-y)]βDGal-O—(CH$_2$)$_5$COOCH$_3$ ∝

| Unit | | x = 2, y = 3 (21) | x = 2, y = 4 (22) | x = 2, y = 6 (23) | x = 3, y = 4 (24) | x = 3, y = 6 (25) | x = 4, y = 6 (26) |
|---|---|---|---|---|---|---|---|
| βDGal 1-4$^x$ | H-1 | 4.49 (8.0) [1.15] | 4.47 (8.0) [1.19] | 4.48 (7.8) [1.10] | 4.49 (8.0) [1.13] | 4.48 (7.9) [1.08] | 4.48 (7.6) [1.09] |
| | H-2 | 3.55 (10.1) [3.0] | 3.36 (9.8) | 3.55 (9.9) [3.7] | 3.56 (9.2) | 3.55 (9.80) [3.4] | 3.54 (9.5) [2.5] |
| | H-3 | 3.68 (3.2) | 3.67 (3.0) | 3.67 | 3.68 (3.7) | 3.67 (3.0) | 3.68 (3.3) [1.54] |
| | H-4 | 3.94 [1.53] | 3.94 [1.60] | 3.93 [1.50] | 3.94 [1.56] | 3.94 [1.52] | 3.94 [1.53] |
| | H-5 | 3.75 | 3.76 | 3.73 | 3.74 | 3.71 | 3.74 |
| | H-6A | 3.77 | 3.77 | 3.80 | 3.80 | 3.80 | 3.77 |
| | H-6B | 3.75 | 3.75 | 3.75 | 3.77 | 3.76 | 3.74 |
| βDGlcNAc 1-x | H-1 | 4.83 (8.9) [1.26] | 4.82 (7.6) [1.37] | 4.83 (8.0) [1.34] | 4.66 (8.4) [1.21] | 4.73 (8.3) [1.18] | 4.69 (8.1) [1.33] |
| | H-2 | 3.64 (10.4) [2.1] | 3.74 | 3.76 | 3.88 (10.2) | 3.81 (10.5) | 3.76 (9.0) |
| | H-3 | 3.72 (8.7) | 3.71 | 3.72 | 3.72$^b$ | 3.75 | 3.72 (8.5) |
| | H-4 | 3.70 (10.3) | 3.71 | 3.70 (9.2) | 3.76$^b$ (9.5) | 3.75 | 3.72 |
| | H-5 | 3.48 [1.08] | 3.52 | 3.56 | 3.61 | 3.60 | 3.54 |
| | H-6A | 3.99 (2.2, 12.5) [0.80] | 3.96 (1, 12.2) [0.73] | 3.98 (1.8, 12.1) [0.71] | 3.90 (2.1, 12.1) [0.76] | 3.97 (2.1, 12.5) [0.80] | 3.98 (2, 12.0) [0.68] |
| | H-6B | 3.88 (4.5) [0.72] | 3.85 (4.6) | 3.83 (5.2) [0.73] | 3.88 (4.6) | 3.86 (4.6) | 3.86 (4.6) [0.70] |
| | OCH$_3$ | 2.12$^a$ | 2.08$^a$ [1.7] | 2.05$^a$ [1.52] | 2.06$^a$ [1.75] | | |
| βBDGal 1-4$^y$ | H-1 | 4.48 (7.7) [1.09] | 4.48 (8.0) [1.15] | 4.48 (7.9) [1.07] | 4.48 (8.0) [1.16] | 4.49 (7.8) [1.11] | 4.48 (7.6) [1.09] |
| | H-2 | 3.56 (10.1) | 3.55 (9.8) | 3.55 (10.0) | 3.56 (9.2) | 3.56 (9.8) | 3.55 (9.2) [3.0] |
| | H-3 | 3.68 (3.2) | 3.67 (3.0) | 3.67 | 3.68 (3.7) | 3.68 (3.0) | 3.68 (3.3) [1.54] |
| | H-4 | 3.94 [1.53] | 3.94 [1.60] | 3.93 [1.50] | 3.94 [1.58] | 3.94 [1.52] | 3.94 [1.53] |
| | H-5 | 3.75 | 3.76 | 3.73 | 3.74 | 3.77 | 3.74 |
| | H-6A | 3.77 | 3.77 | 3.8 | 3.80 | 3.80 | 3.77 |
| | H-6B | 3.75 | 3.75 | 3.75 | 3.77 | 3.76 | 3.74 |
| βDGlcNAc 1-y | H-1 | 4.77 (7.7) [1.22] | 4.73 (8.0) [1.11] | 4.56 (8.2) [1.115] | 4.98 (8.4) [1.28] | 4.70 (8.1) [1.16] | 4.55 (8.2) [1.12] |
| | H-2 | 3.74 (10.5) | 3.76 | 3.76 | 3.81 (10.1) | 3.77 (10.5) | 3.77 (9.6) |
| | H-3 | 3.81 (8.9) | 3.73 | 3.73 | 3.75 (9) | 3.72 | 3.72 (9) |
| | H-4 | 3.74 | 3.72 | 3.71 (9.5) | 3.71 (9.2) | 3.72 | 3.72 |
| | H-5 | 3.56 | 3.58 | 3.60 | 3.57 | 3.61 | 3.60 |
| | H-6A | 3.96 (2.5, 12.5) [0.74] | 4.00 (2, 12.1) [0.77] | 4.00 (2.4, 12.1) | 3.99 (2.2, 12.1) [0.76] | 4.01 (2.2, 12.2) | 4.00 (2.0, 12.2) |
| | H-6B | 3.86 (4.5) [0.75] | 3.83 (5.5) | 3.84 (5.2) [0.73] | 3.84 (5.5) | 3.85 (5.2) | 3.86 (4.7) |
| | OCH$_3$ | 2.09$^a$ | 2.05 [1.6] | 2.03$^a$ [1.40] | 2.05$^a$ [1.67] | | |
| βDGal 1-O | H-1 | 4.59 (8.1) [1.11] | 4.49 (7.9) [1.23] | 4.44 (7.7) [1.10] | 4.36 (7.9) [1.28] | 4.36 (7.9) [1.17] | 4.35 (7.8) [1.28] |
| | H-2 | 3.89 (10.5) | 3.49 (9.5) [1.85] | 3.62 (9.1) [1.70] | 3.39 (9.6) [3.0] | 3.55 (9.9) [3.4] | 3.36 (9.6) [2.6] |
| | H-3 | 4.00 (3.0) [1.14] | 3.82 (3.0) | 3.68 (3.3) | 3.69 (2.4) | 3.70 (3.0) | 3.71 (2.1) |
| | H-4 | 4.15 [1.42] | 4.03 [1.28] | 3.85 [0.99] | 4.30 [1.22] | 4.12 [1.40] | 4.01 [1.08] |
| | H-5 | 3.66 | 3.65 | 3.74 | 3.66 | 3.78 | 3.77 |
| | H-6A | 3.78 | 3.78 | 4.00 | 3.79 | 4.04 | 4.09 [0.77] |
| | H-6B | 3.75 | 3.74 | 3.75 | 3.74 | 3.77 | 3.79 |
| (CH$_2$)$_5$COOCH$_3$ | H-1A | 3.92 | 3.88 | 3.88 | 3.87 | 3.90 | 3.86 |
| | H-1B | 3.69 | 3.67 | 3.66 | 3.64 | 3.65 | 3.61 |
| | H$_2$2 | 1.65 [0.61] | 1.64 [0.58] | 1.64 [0.69] | 1.63 [0.65] | 1.65 [0.71] | 1.63 |
| | H$_2$3 | 1.41 [0.65] | 1.40 [0.65] | 1.41 [0.62] | 1.38 [0.69] | 1.41 [0.69] | 1.40 [0.74] |
| | H$_2$4 | 1.65 [0.73] | 1.64 [0.75] | 1.65 [0.70] | 1.63 [0.78] | 1.65 [0.79] | 1.64 |
| | H$_2$5 | 2.43 [0.98] | 2.43 [0.95] | 2.43 [0.90] | 2.41 [1.03] | 2.43 [1.00] | 2.42 [1.02] |

TABLE 4-continued $^1$H Chemical shifts of the pentasaccharides
βDGal(1-4)βDGlcNAc(1-x)[βDGal(1-4)βDGlcNAc(1-y)]βDGal-O—(CH$_2$)$_5$COOCH$_3$∝

| Unit | | x = 2, y = 3 (21) | x = 2, y = 4 (22) | x = 2, y = 6 (23) | x = 3, y = 4 (24) | x = 3, y = 6 (25) | x = 4, y = 6 (26) |
|---|---|---|---|---|---|---|---|
| | OCH$_3$ | 3.70 | 3.70 [1.9] | 3.71 [1.71] | 3.70 [1.92] | 3.71 | 3.69 |

∝ The hydrogen chemical shifts are expressed relative to HOD (4.83 ppm, δ acetone 2.23 ppm). The vicinal hydrogen-hydrogen coupling constants in hertzs and the proton spin-lattice relaxation times (T$_1$) in seconds are shown in the parenthesis and brackets, respectively.
a,b,cThese assignments may be interchanged.

TABLE 5

$^{13}$C Chemical shift of the pentasaccharides
βDGal(1-4)βDGlcNAc(1-x)[βDGal(1-4)βDGlcNAc(1-y)]βDGal-O—(CH$_2$)$_5$COOCH$_3$∝

| Unit | | x = 2, y = 3 (21) | x = 2, y = 4 (22) | x = 2, y = 6 (23) | x = 3, y = 4 (24) | x = 3, y = 6 (25) | x = 4, y = 6 (26) |
|---|---|---|---|---|---|---|---|
| βDGal 1-4$^x$ | C-1 | 103.5 (0.34) | 103.5 (0.36) | 103.6 (0.37)$^a$ | 103.6 (0.35*) | 103.6 (0.40)$^a$ | 103.6 (0.37)$^a$ |
| | C-2 | 71.6 (0.35)$^a$ | 71.6 (0.37) | 71.6 (0.39) | 71.6 (0.36)$^a$ | 71.6 (0.40*) | 71.6 (0.37*) |
| | C-3 | 73.1 (0.35) | 73.2 (0.37) | 73.2 (0.39) | 73.2 (0.35*) | 73.2 (0.40*) | 73.2 (0.38*) |
| | C-4 | 69.2 (0.30)$^b$ | 69.2 (0.37) | 69.2 (0.30) | 69.2 (0.30) | 69.2 (0.29*) | 69.2 (0.31*) |
| | C-5 | 76.0 (0.34) | 76.0 (0.36) | 76.0 (0.39) | 76.1 (0.36)$^b$ | 76.0 (0.47) | 76.0 (0.37*) |
| | C-6 | 61.7 (0.23)$^c$ | 61.6 (0.26) | 61.6 (0.27)$^c$ | 61.7 (0.25)$^c$ | 61.7 (0.28) | 61.7 (0.26*) |
| βDGlcNAc 1-x | C-1 | 99.5 (0.25) | 101.7 (0.23) | 102.1 (0.29) | 103.8 (0.28) | 103.3 (0.31*) | 102.5 (0.28) |
| | C-2 | 57.0 (0.24) | 56.2 (0.25) | 56.2 (0.27)$^c$ | 56.1 (0.29) | 55.9 (0.28) | 55.9 (0.28) |
| | C-3 | 72.6 (0.27) | 73.0 (0.26)$^a$ | 73.0 (0.32)$^d$ | 73.2 (0.35*) | 72.9 (0.31) | 73.1 (0.30*) |
| | C-4 | 79.2 (0.25) | 80.0 (0.27)$^b$ | 79.2 (0.31)$^e$ | 79.0 (0.30) | 78.9 (0.30) | 79.1 (0.30)$^b$ |
| | C-5 | 75.5 (0.25) | 75.4 (0.27)$^c$ | 75.5 (0.28) | 75.3 (0.28) | 75.3 (0.36) | 75.1 (0.28) |
| | C-6 | 60.5 (0.14) | 60.9 (0.17) | 60.9 (0.15) | 60.7 (0.16) | 60.6 (0.16) | 60.8 (0.16) |
| | CON | 175.3 (1.1)$^d$ | 175.3 (. . .)$^e$ | 175.4 (1.2)$^f$ | 175.3 (1.2)$^d$ | 175.6 (. . .)$^b$ | 175.4 (1.2)$^c$ |
| | OCH$_3$ | 23.5 (0.16)$^e$ | 23.3 (0.9)$^f$ | 22.9 (1.2)$^g$ | 23.1 (1.1)$^e$ | 23.0 (1.4)$^c$ | 23.0 (1.1)$^d$ |
| βDGal 1-4$^y$ | C-1 | 103.6 (0.34) | 103.6 (0.37) | 103.6 (0.37)$^a$ | 103.6 (0.35*) | 103.6 (0.42)$^a$ | 103.5 (0.36)$^a$ |
| | C-2 | 71.6 (0.34)$^a$ | 56.0 (0.25) | 71.6 (0.39) | 71.7 (0.36)$^a$ | 71.6 (0.40*) | 71.6 (0.37*) |
| | C-3 | 73.1 (0.35) | 73.2 (0.37) | 73.2 (0.39) | 73.2 (0.35*) | 73.2 (0.40*) | 73.2 (0.38*) |
| | C-4 | 69.2 (0.27)$^b$ | 69.2 (0.37) | 69.2 (0.30) | 69.2 (0.30) | 69.2 (0.29*) | 69.2 (0.31*) |
| | C-5 | 76.0 (0.34) | 76.0 (0.36) | 76.0 (0.39) | 76.0 (0.36)$^b$ | 76.0 (0.47) | 76.0 (0.37*) |
| | C-6 | 61.6 (0.24)$^c$ | 61.6 (0.26) | 61.6 (0.27)$^b$ | 61.7 (0.25)$^c$ | 61.7 (0.28) | 61.7 (0.268) |
| βDGlcNAc 1-y | C-1 | 102.0 (0.27) | 102.4 (0.28) | 101.9 (0.31*) | 101.8 (0.27) | 102.0 (0.33*) | 102.0 (0.30) |
| | C-2 | 56.5 (0.25) | 56.0 (0.25) | 55.7 (0.31)$^c$ | 55.5 (0.26) | 55.7 (0.28) | 55.6 (0.29) |
| | C-3 | 72.8 (0.28) | 72.8 (0.31)$^a$ | 73.0 (0.32)$^d$ | 73.1 (0.27) | 73.1 (0.32) | 73.1 (0.30*) |
| | C-4 | 78.9 (0.26) | 79.2 (0.25)$^b$ | 79.2 (0.29)$^e$ | 79.4 (0.28) | 79.2 (0.31) | 79.1 (0.28)$^b$ |
| | C-5 | 75.5 (0.27) | 75.1 (0.29)$^c$ | 75.4 (0.32) | 75.3 (0.27) | 75.4 (0.26) | 75.4 (. . .) |
| | C-6 | 60.4 (0.15) | 60.9 (0.17) | 60.9 (0.16) | 60.7 (0.16) | 60.6 (0.16) | 60.7 (0.15) |
| | CON | 175.1 (1.1)$^d$ | 175.0 (. . .)$^e$ | 175.0 (1.3)$^f$ | 175.2 (1.2)$^d$ | 175.0 (0.9)$^b$ | 174.8 (1.3)$^c$ |
| | OCH$_3$ | 23.2 (. . .)$^e$ | 23.0 (0.9)$^f$ | 22.9 (1.2)$^g$ | 23.0 (1.1)$^e$ | 22.9 (0.5)$^c$ | 22.9 (1.1)$^d$ |
| βDGal 1-O | C-1 | 101.2 (0.26) | 101.6 (0.23) | 101.9 (0.31*) | 103.5 (0.28) | 103.3 (0.31*) | 103.2 (0.28) |
| | C-2 | 75.4 (0.23) | 79.0 (0.23) | 79.1 (0.29) | 70.4 (0.26) | 70.3 (0.28) | 71.4 (0.27) |
| | C-3 | 81.5 (0.24) | 74.0 (0.23) | 73.6 (0.28) | 83.6 (0.23) | 82.8 (0.33) | 73.4 (0.26) |
| | C-4 | 69.5 (—) | 76.7 0.26 | 69.5 (0.27) | 75.7 (0.23) | 69.3 (0.29) | 77.3 (0.250) |
| | C-5 | 75.1 (0.26) | 74.6 (0.26) | 73.9 (0.29) | 74.6 (0.26) | 74.0 (0.31) | 73.8 (0.25) |
| | C-6 | 61.4 (0.21) | 61.1 (0.20) | 69.3 (0.29) | 61.2 (0.21) | 70.0 (0.12) | 70.5 (0.15) |
| (CH$_2$)$_5$COOCH$_3$ | CH$_2$1 | 70.6 (0.24) | 70.5 (0.24) | 70.7 (0.25) | 70.7 (0.28) | 70.7 (0.26) | 70.5 (0.24) |
| | CH$_2$2 | 29.2 (0.30) | 29.1 (0.29) | 29.1 (0.33) | 29.0 (0.38) | 29.0 (0.37) | 29.0 (0.33) |
| | CH$_2$3 | 25.3 (0.43) | 25.2 (0.53) | 25.3 (0.48) | 25.2 (0.62) | 25.3 (0.49) | 25.3 (0.57) |
| | CH$_2$4 | 24.7 (0.57) | 24.7 (0.68) | 24.8 (0.62) | 24.7 (0.75) | 24.7 (0.84) | 24.7 (0.71) |
| | CH$_2$5 | 34.3 (0.67) | 34.3 (0.75) | 34.3 (0.73) | 34.3 (0.95) | 34.3 (1.12) | 34.2 (0.88) |
| | COO | 178.2 (. . .) | | 178.2 (. . .) | 178.3 (. . .) | | 178.3 (. . .) |
| | OCH$_3$ | 52.7 (2.1) | 52.7 (1.7) | 52.8 (. . .) | 52.8 (2.7) | 52.8 (—) | 52.8 (2.6) |

∝ The carbon chemical shifts are expressed relative to 1,4-dioxane, using the deuterium lock of the spectrometer, which set the chemical shift of dioxane at 66.9 ppm. The spin-lattice relaxation times (T$_1$) in seconds are given in the parenthesis.
a,b,c,d,e,f,gThese shifts may be interchanged
*Could not be determined precisely due to signal overlap.

TABLE 6

$^1$H Chemical shifts of the heptaaccharides aDNeuAc(2-6)βDGal(1-4)βDGlcNAc(1-x)-[aDNeuAc(2-6)βDGal(1-4)βDGlcNAc-(1-y)]βDGal-O—(CH$_2$)$_5$COOCH$_3$$^a$

| Unit | | x = 2, y = 3 (27) | x = 2, y = 4 (28) | x = 2, y = 6 (29) | x = 3, y = 6 (30) | x = 4, y = 6 (31) |
|---|---|---|---|---|---|---|
| aDNeuAc 2-6$^x$ | H-3eq | 2.68 (5.0, 12.4) | 2.68 (4.7, 12.3) [0.65] | 2.67 (4.6, 12.2) [0.54] | 2.68 (4.7, 12.4) [0.73] | 2.68 (4.6, 12.4) [1.38] |
| | H-3ax | 1.72 (12.4) | 1.71 (12.3) [0.63] | 1.72 (12.2) [0.58] | 1.73 (12.4) [0.72] | 1.73 (12.4) [0.74] |
| | H-4 | 3.66 | 3.66 | 3.66 | 3.66 (10) | 3.66 |
| | H-5 | 3.81 (10.1) | 3.80 (10.0) | 3.80 | 3.82 (10.1) | 3.80 (10.2) |
| | H-6 | 3.71 | 3.70 | 3.70 | 3.72 | 3.71 (1.5) |
| | H-7 | 3.57 | 3.56 | 3.56 | 3.55 | 3.56 |
| | H-8 | 3.89 | 3.89 | 3.89 | 3.90 | 3.88 |
| | H-9A | 3.88 | 3.88 | 3.88 | 3.89 | 3.89 |
| | H-9B | 3.64 | 3.64 | 3.64 | 3.65 | 3.64 |
| βDGal 1-4$^x$ | H-1 | 4.45 (7.8) | 4.45 (7.9) [1.30]$^b$ | 4.45 (8) | 4.46 (8.0) [1.57] | 4.46 (8.0) [1.56] |
| | H-2 | 3.54 (9.7) | 3.54 [1.8]$^c$ | 3.54 (10) | 3.55 (9.9) | 3.55 (9.80$^a$ |

TABLE 6-continued $^1$H Chemical shifts of the heptaaccharides aDNeuAc(2-6)βDGal(1-4)βDGlcNAc(1-x)-[aDNeuAc(2-6)βDGal(1-4)βDGlcNAc-(1-y)]βDGal-O—(CH$_2$)$_5$COOCH$_3$$^a$

| Unit | | x = 2, y = 3 (27) | x = 2, y = 4 (28) | x = 2, y = 6 (29) | x = 3, y = 6 (30) | x = 4, y = 6 (31) |
|---|---|---|---|---|---|---|
| | H-3 | 3.66 (3.1) | 3.67 | 3.68 (2.7) | 3.68 (350 | 3.68 (3.5) |
| | H-4 | 3.92 | 3.93 | 3.93 | 3.93 | 3.93 |
| | H-5 | 3.83 | 3.82 | 3.83 | 3.84 | 3.83 |
| | H-6A | 3.99 | 3.99 | 4.00 | 4.01 | 3.99 |
| | H-6B | 3.56 | 3.56 | 3.56 | 3.56 | 3.55 |
| βDGlcNAc 1-x | H-1 | 4.74 (8.2) | 4.85 (8.5) [1.54] | 4.85 (8.0) [1.58] | 4.74 (8.2) [1.72] | 4.72 (8.4) [1.81] |
| | H-2 | 3.71 | 3.76 | 3.76 | 3.80 | 3.76 |
| | H-3 | 3.79 | 3.76 | 3.76 | 3.79 | 3.76 |
| | H-4 | 3.61 (9.9) | 3.62 | 3.62 | 3.67 | 3.66 |
| | H-5 | 3.44 | 3.53 | 3.58 | 3.61 | 3.66 |
| | H-6A | 3.99 (2.2, 12.2) | 3.96 (<2,12.3) | 3.98 (<2, 12.4) | 3.96 (<2, 12.2) | 3.56 |
| | H-6B | 3.85 (3.0) | 3.83 (5.2) | 3.83 (5.4) | 3.86 (4.5) | 3.98 (1.6, 12.2) |
| | OCH$_3$ | 2.15$^b$ | 210$^d$ | 2.07$^b$ | 2.06$^b$ | 3.85 (5.0) |
| aDNeuAc2-6$^y$ | H-3eq | 2.67 (5.0, 12.4) | 2.67 (4.6, 12.3) [0.65] | 2.67 (4.6, 12.2) [0.54] | 2.68 (4.7, 12.4) [0.73] | 2.68 (4.6,12.4) |
| | H-3ax | 1.71 (12.4) | 1.71 (12.4) [0.63] | 1.71 (12.2) [0.58] | 1.72 (12.4) [0.72] | 1.72 (12.4) [0.74] |
| | H-4 | 3.66 | 3.66 | 3.66 | 3.66 (10) | 3.66 |
| | H-5 | 3.81 (10.1) | 3.80 (10.0) | 3.80 | 3.81 (10.1) | 3.80 (10.2) |
| | H-6 | 3.71 | 3.70 | 3.70 | 3.72 | 3.71 (1.5) |
| | H-7 | 3.57 | 3.56 | 3.56 | 3.55 | 3.56 |
| | H-8 | 3.89 | 3.89 | 3.89 | 3.90 | 3.88 |
| | H-9A | 3.88 | 3.88 | 3.88 | 3.89 | 3.89 |
| | H-9B | 3.64 | 3.64 | 3.64 | 3.65 | 3.64 |
| βDGal 1-4$^y$ | H-1 | 4.43 (8.0) | 4.45 (7.9) [1.31]$^b$ | 4.45 (8) | 4.46 (8.0) [1.54] | 4.45 (8.0) [1.56] |
| | H-2 | 3.57 (9.7) | 3.54 [1.8]$^b$ | 3.54 (10) | 3.55 (9.9) | 3.54 (9.70$^a$ |
| | H-3 | 3.66 (3.1) | 3.67 | 3.68 (2.7) | 3.68 (3.50 | 3.68 (3.5) |
| | H-4 | 3.92 | 3.93 | 3.93 | 3.93 | 3.93 |
| | H-5 | 3.83 | 3.82 | 3.83 | 3.84 | 3.83 |
| | H-6A | 3.99 | 3.99 | 4.00 | 4.01 | 3.99 |
| | H-6B | 3.56 | 3.56 | 3.56 | 3.56 | 3.55 |
| βDGlcNAc 1-y | H-1 | 4.69 | 4.76 (7.8) [1.58] | 4.59 (8.3) [1.28] | 4.59 (8.4) [1.57] | 4.57 (8.00) [1.51] |
| | H-2 | 3.81 | 3.79 | 3.76 | 3.76 | 3.75 |
| | H-3 | 3.81 | 3.78 | 3.76 | 3.77 | 3.75 |
| | H-4 | 3.70 | 3.63 | 3.63 | 3.64 | 3.66 (9.5) |
| | H-5 | 3.56 | 3.60 | 3.63 | 3.65 | 3.61 |
| | H-6A | 3.93 (<2, 12.2) | 3.99 (<2, 12.2) | 4.00 (<2, 12.2) | 4.01 (<2, 12.5) | 4.00 (2.2, 12) |
| | H-6B | 3.86 (4.5) | 3.88 (5.3) | 3.83 (4.9) | 3.83 (4.4) | 3.85 (5.5) |
| | OCH$_3$ | 2.11$^b$ | 2.08$^d$ | 2.05$^b$ | 2.06$^b$ | 2.05$^b$ |
| βDGal 1-O | H-1 | 4.55 (8.0) | 4.48 (7.8)[1.32] | 4.45 (8) | 4.37 (8.0) [1.39] | 4.35 (8.00 [1.56] |
| | H-2 | 3.84 (9.7) | 3.50 (9.9) [1.94] | 3.63 | 3.55 (9.5) | 3.37 (9.5) |
| | H-3 | 3.99 (3.5) | 3.82 (3.5) | 3.70 (3.5) | 3.71 (3.6) | 3.72 (3.0) |
| | H-4 | 4.14 | 4.05 (0.6) [1.38] | 3.85 | 4.13 [1.68] | 4.02 |
| | H-5 | 3.67 | 3.65 | 3.76 | 3.78 | 3.78 |
| | H-6A | 3.85 | 3.75 | 4.00 | 4.04 | 4.11 [1.41] |
| | H-6B | 3.73 | 3.66 | 3.77 | 3.78 | 3.79 |
| (CH$_2$)$_5$COOCH$_3$ | H-1A | 3.91 | 3.87 | 3.88 | 3.89 | 3.87 |
| | H-1B | 3.69 | 3.67 | 3.67 | 3.64 | 3.61 |
| | H$_2$-2 | 1.65 | 1.63 | 1.66 | 1.65 | 1.64 |
| | H$_2$-3 | 1.41 | 1.39 | 1.42 | 1.41 | 1.40 |
| | H$_2$-4 | 1.66 | 1.64 | 1.65 | 1.65 | 1.64 |
| | H$_2$-5 | 2.43 | 2.42 | 2.43 | 2.43 | 2.42 |
| OCH$_3$ | | 3.70 | 3.71 | 3.71 | 3.71 | 3.70 |

$^a$The hydrogen chemical shifts are expressed relative to HOD (4.83 ppm, ∂ acetone 2.23 ppm). The vicinal hydrogen-hydrogen coupling constants in hertzs and the proton spin-lattice relaxation times (T$_1$) in seconds are shown in the parenthesis and brackets, respectively.
$^{b,c,d}$These assignments may be reversed.

TABLE 7

$^{13}$C Chemical shifts of the heptaaccharides aDNeuAc(2-6)βDGal(1-4)βDGlcNAc(1-x)[aDNeuAc(2-6)βDGal(1-4)βD-GlcNAc-(1-y)]βDGal-O—(CH$_2$)$_5$COOCH$_3$ ∞

| Unit | | x = 2, y = 3 (27) | x = 2, y = 4 (28) | x = 2, y = 6 (29) | x = 3, y = 6 (30) | x = 4, y = 6 (31) |
|---|---|---|---|---|---|---|
| aDNeuAc 2-6$^x$ | C-2 | 100.8 | | 100.8 | 101.0 | 100.8 |
| | C-3 | 40.7 | 40.8 | 40.6 | 40.8 [0.16] | 40.8 |
| | C-4 | 68.8$^a$ | 68.9 | 68.8 | 68.9 [0.31] | 69.9 |
| | C-5 | 52.5 | 52.5 | 52.5 | 52.5 [0.31] | 52.6 |
| | C-6 | 73.2 | 73.2 | 73.2 | 73.2 [0.31] | 73.2 |
| | C-7 | 69.0 | 69.1 | 69.0 | 69.1 [0.28] | 69.1 |
| | C-8 | 72.4 | 72.4 | 72.3 | 72.4 [0.34] | 72.4 |
| | C-9 | 63.3 | 63.3 | 63.3 | 63.3 [0.23] | 63.3 |
| βDGal 1-4$^x$ | C-1 | 104.1 | 104.1 | 104.2 | 104.2 [0.30] | 104.1 |
| | C-2 | 71.3 | 71.4 | 71.4 | 71.4 [0.30] | 71.4 |
| | C-3 | 73.0 | 73.1 | 73.1 | 73.1 [0.30] | 73.1 |
| | C-4 | 69.0 | 69.1 | 69.0 | 69.0 [0.28] | 69.1 |
| | C-5 | 72.3 | 74.3 | 74.3 | 74.3 [0.28] | 74.3 |

TABLE 7-continued $^{13}$C Chemical shifts of the heptaacchardies
aDNeuAc(2-6)βDGal(1-4)βDGlcNAc(1-x)[aDNeuAc(2-6)βDGal(1-4)βD-GlcNAc-(1-y)]βDGal-O—(CH$_2$)$_5$COOCH$_3$ α

| Unit | | x = 2, y = 3 (27) | x = 2, y = 4 (28) | x = 2, y = 6 (29) | x = 3, y = 6 (30) | x = 4, y = 6 (31) |
|---|---|---|---|---|---|---|
| | C-6 | 63.9 | 64.0 | 63.9 | 64.0 [0.17] | 64.0 |
| βDGlcNAc 1-x | C-1 | 99.8 | 101.7 | 101.9 | 103.1 [0.30] | 102.4 |
| | C-2 | 56.4 | 55.9 | 55.9 | 55.7 [0.26] | 55.7 |
| | C-3 | 72.7 | 73.0 | 73.1 | 73.0 [0.29] | 73.2 |
| | C-4 | 81.6 | 81.4 | 81.5 | 81.1 [0.30] | 81.3 |
| | C-5 | 75.3 | 75.1 | 75.2 | 75.0 [0.28] | 74.9 |
| | C-6 | 60.8 | 61.2 | 61.2 | 60.8 [0.17] | 61.0 |
| | CONOCH$_3$ | 23.6$^b$ | 23.4 | 23.0 | 23.1 [0.88] | 23.1 |
| aDNeuAc 2-6$^y$ | C-2 | 100.8 | | 100.8 | 101.0 | 100.8 |
| | C-3 | 40.7 | 40.8 | 40.6 | 40.8 [0.16] | 40.8 |
| | C-4 | 68.8$^a$ | 68.9 | 68.8 | 68.9 [0.30] | 69.9 |
| | C-5 | 52.5 | 52.5 | 52.5 | 52.5 [0.31] | 52.6 |
| | C-6 | 73.2 | 73.2 | 73.2 | 73.2 [0.31] | 73.2 |
| | C-7 | 69.0 | 69.1 | 69.0 | 69.1 [0.28] | 69.1 |
| | C-8 | 72.4 | 72.4 | 72.3 | 72.4 [0.34] | 72.4 |
| | C-9 | 63.3 | 63.3 | 63.3 | 63.3 [0.23] | 63.3 |
| βDGal 1-4$^y$ | C-1 | 104.4 | 104.1 | 104.2 | 104.2 [0.31] | 104.2 |
| | C-2 | 71.3 | 71.4 | 55.4 | 71.4 [0.30] | 71.4 |
| | C-3 | 73.0 | 73.1 | 73.1 | 73.1 [−0.30] | 73.1 |
| | C-4 | 69.0 | 69.1 | 69.0 | 69.0 [0.28] | 69.1 |
| | C-5 | 74.3 | 74.3 | 74.3 | 74.3 [0.28] | 74.3 |
| | C-6 | 63.8 | 64.0 | 63.9 | 64.0 [0.17] | 64.0 |
| βDGlcNAc 1-y | C-1 | 102.2 | 102.2 | 101.7 | 101.8 [0.26] | 101.9 |
| | C-2 | 56.2 | 55.8 | 71.4 | 55.5 [0.28] | 55.4 |
| | C-3 | 72.8 | 73.0 | 73.1 | 73.1 [0.32] | 73.2 |
| | C-4 | 80.9 | 81.4 | 81.4 | 81.4 [0.27] | 81.4 |
| | C-5 | 75.2 | 74.9 | 75.0 | 75.1 [0.28] | 75.1 |
| | C-6 | 60.6 | 61.2 | 61.0 | 61.0 [0.18] | 61.0 |
| | CONOCH$_3$ | 23.2$^b$ | 23.1 | 23.0 | 23.0 [1.2] | 23.0 |
| βDGal 1-O | C-1 | 101.3 | 101.6 | 101.9 | 103.2 [0.30] | 103.1 |
| | C-2 | 74.7 | 78.9 | 79.1 | 70.3 [0.29] | 71.5 |
| | C-3 | 81.5 | 74.3 | 73.5 | 82.9 [0.27] | 73.4 |
| | C-4 | 69.7 | 76.6 | 69.5 | 69.2 [0.26] | 77.3 |
| | C-5 | 75.0 | 74.6 | 73.8 | 74.0 [0.29] | 73.3 |
| | C-6 | 61.3 | 61.2 | 69.2 | 70.0 [0.13] | 70.5 |
| (CH$_2$)$_5$COOCH$_3$ | CH$_2$-1 | 70.6 | 70.5 | 70.8 | 70.7 [0.31] | 70.5 |
| | CH$_2$-2 | 29.0 | 29.0 | 29.1 | 29.0 [0.36] | 29.0 |
| | CH$_2$-3 | 25.2 | 25.2 | 25.4 | 25.3 [0.56] | 25.3 |
| | CH$_2$-4 | 24.6 | 24.7 | 24.7 | 24.7 [0.69] | 24.7 |
| | CH$_2$-5 | 34.3 | 34.3 | 34.3 | 34.3 [0.88] | 34.3 |
| | COOOCH$_3$ | 52.7 | 52.7 | 52.8 | 52.7 [2.5] | 52.8 |

α The carbon chemical shifts are expressed to 1,4-dioxane. using the deuterium lock of the spectrometer, which set the chemical shift of dioxane at 66.9 ppm. The spin-lattice relaxation times (T$_1$) in second are given in the parenthesis for the heptasaccharide 25.
$^{a,b,c,d,e,f,g}$These assignments may be reversed.
*Could not be determined precisely due to signal overlap.

TABLE 8

Inhibition of Influenza Virus Adsorbtion to Erythrocytes by Cluster Sialosides

| Compound | Concentration for 50% Inhibition$^a$ (mM) | Relative Potency |
|---|---|---|
| Me αDNeuAc$^b$ | 1.9 | 1.0 |
| Example 27 | 0.25 | 7.2 |
| Example 28 | 1.3 | 1.5 |
| Example 29 | 0.38 | 4.8 |
| Example 29 | 0.18 | 10 |
| Example 30 | 0.23 | 8.4 |
| Example 33 | <0.12 | >14.4 |
| Example 28A | 0.95 | 1.9 |

$^a$Inhibition of influenza virus (A/Aichi/2/68) to resialylated erythrocytes was examined as described by Pritchett et al. (Virology, 1987, 160, 502-506).
$^b$Methyl 5-acetamido-3,5-dideoxy-α-D-glycero-D-galacto-nanulo-pyranoside.

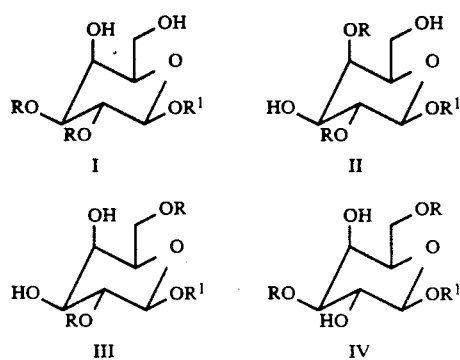

What is claimed is:
1. A compound comprising the formula I, II, III, IV, V, or VI

47

[Structures V and VI shown:
V: pyranose ring with OR, OR at top, HO, HO on left, OR¹ on right
VI: pyranose ring with OR⁷, OR⁸ at top, R⁶O, R⁵O on left, OR¹ on right]

wherein
R¹ is $(CH_2)_nCOOR^2$ or $(CH_2)_nCONHR^3NHC(O)R^4$;
n is an integer from 1 to 20;
R² is a $C_1$ to $C_6$ alkyl or aralkyl;
R³ is a $C_1$ to $C_4$ alkyl;
R⁴ is $OCH_2C_6H_5$ or alkenyl;
R⁵, R⁶, R⁷, and R⁸ are each independently H, $C_6H_5CH$, allyl, tertbutyldimethylsilyl or 2-deoxy-2-phthalimido- 3,4,6-tri-O-acetyl-β-D-glucopyranosyl; and
R is a monosaccharide selected from the group consisting of glucosamine, N-protected glucosamine, and O-protected glucosamine,
a disaccharide consisting of galactose glycosidically linked to N-acetylglucosamine, or
a trisaccharide consisting of N-acetylneuraminic acid glycosidically linked to galactose which in turn is glycosidically linked to N-acetylglucosamine.

2. The compound of claim 1 wherein R is a monosaccharide.

3. The compound of claim 2 which is:
5-(methoxycarbonyl)pentyl 2,3-di-O-(2-acetamido-2-deoxy-β-D-glucopyranosyl)-β-D-galactopyranoside;
5- methoxycarbonyl)pentyl 2,4-di-O-(2-acetamido-2-deoxy-β-D-glucopyranosyl)-β-D-galactopyranoside;
5-(methoxycarbonyl)pentyl 2,6-di-O-(2-acetamido-2-deoxy-β-glucopyranosyl)-B-D-galactopyranoside;
5-(methoxycarbonyl)pentyl 3,6-di-O-(2-acetamido-2-deoxy-β-D-glucopyranosyl)-β-D-galactopyranoside; and
5- methoxycarbonyl)pentyl 4,6-di-O-(2-acetamido-2-deoxy-β-D-glucopyranosyl)-β-D-galactopyranoside.

4. The compound of claim 1 wherein R is a disaccharide.

5. The compound of claim 4 which is:
5-(methoxycarbonyl)pentyl 2,3-di-O-{β-D-galactopyranosyl-(1→4)-2-acetamido-2-deoxy-β-D-glucopyranosyl}-β-D-galactopyranoside;
5-(methoxycarbonyl)pentyl 2,4-di-O-{β-D-galactopyranosyl-(1→4)-2-acetamido-2-deoxy-β-D-glucopyranosyl}-β-D-galactopyranoside;
5-(methoxycarbonyl)pentyl 2,6-di-O-{β-D-galactopyranosyl-(1→4)-2-acetamido-2-deoxy-β-D-glucopyranosyl}-β-D-galactopyranoside;
5-(methoxycarbonyl)pentyl 3,6-di-O-{β-D-galactopyranosyl(1→4)-2-acetamido-2-deoxy-β-D-glucopyranosyl}-βD-galactopyranoside; and
5-(methoxycarbonyl)pentyl 4,6-di-O-{β-D-galactopyranosyl(1→4)-2-acetamido-2-deoxy-β-D-glucopyranosyl}-β-D-galactopyranoside.

6. The compound of claim 1 wherein R is a trisaccharide.

7. The compound of claim 6 which is:
5-(methoxycarbonyl)pentyl 2,3-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside;
5-(methoxycarbonyl)pentyl 2,4-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside;

48

5-(methoxycarbonyl)pentyl 2,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside;
5-(methoxycarbonyl)pentyl 3,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside; and
5-(methoxycarbonyl)pentyl 4,6-di-O-{5-acetamido-3,5-dideoxy-D-glycero-D-galacto-2-nanulopyranosylonic acid(2→6)-β-D-galactopyranosyl(1→4)-2-acetamido-2-deoxy-β-D-glucopyranosyl}-β-D-galactopyranoside.

8. A compound of claim 1 of formula VI.

9. A compound of claim 8 which is:
5-(Methoxycarbonyl)pentyl 3-O-allyl-β-D-galactopyranoside;
5-(Methoxycarbonyl)pentyl 3-O-allyl-6-(t-butyldimethylsilyl)-β-D-galactopyranoside;
5-(Methoxycarbonyl)pentyl 2,6-di-O-allyl-β-D-galactopyranoside;
5-(Methoxycarbonyl)pentyl 2,4-di-O-benzoyl-β-D-galactopyranoside;
5-(Methoxycarbonyl)pentyl 2,3-di-O-allyl-β-D-galactopyranoside;
5-(Methoxycarbonyl)pentyl 4,6-O-benzylidene-2,3-di-O-(2-deoxy-3,4,6-tri-O-acetyl-2-phthalimido-β-D-glucopyranosyl)-β-D-galactopyranoside;
5-(Methoxycarbonyl)pentyl 3-O-allyl-6-O-(t-butyldimethylsilyl)-2,4-di-O-(2-deoxy-3,4,6-tri-O-acetyl-2-phthalimido-β-D-glucopyranosyl)-β-D-galactopyranoside;
5-(Methoxy-carbonyl)pentyl 2,6-di-O-(2-deoxy-3,4,6-tri-O-acetyl-2-phthalimido-β-D-glucopyranosyl)-3,4-O-isopropylidene-β-D-galactopyranoside;
5-(Methoxy-carbonyl)pentyl 2,6-di-O-allyl-3,4-di-O-(2-deoxy-3,4,6-tri-O-acetyl-2-phthalimido-β -D-glycopyranosyl)-β-D-galactopyranoside;
5-(Methoxy-carbonyl)pentyl 2,4-di-O-benzoyl-3,6-di-O-(2-deoxy-3,4,6-tri-O-acetyl-2-phthalimido-β-D-glucopyranosyl)-β-D-galactopyranoside; and
5-(Methoxy-carbonyl)pentyl 2,3-di-O-allyl-4,6-di-O-(2-deoxy-3,4,6-tri-O-acetyl-2-phthalimido-β-D-glucopyranosyl)-β-D-galactopyranoside.

10. The compound of claim 1 wherein the N-protected glucosamine is protected by an acyl, acetyl or phthalimido group.

11. The compound of claim 1 wherein the O-protected glucosamine is protected by an acetyl or acyl groups.

12. A compound comprising the formula VII

[Structure VII: pyranose ring with OR¹⁰, OH at top, HO on left, R⁹O at bottom, OR¹ on right]

wherein
R¹ is $(CH_2)_nCOOR^2$ or $(CH_2)_nCONHR^3NHC(O)R^4$;

n is an integer from 1 to 20;

$R^2$ is a $C_1$ to $C_6$ alkyl or aralkyl;

$R^3$ is a $C_1$ to $C_4$ alkyl;

$R^4$ is $OCH_2C_6H_5$ or O-alkenyl;

$R^9$ is a trisaccharide consisting of N-acetylneuraminic acid glycosidically linked to galactose which in turn is glycosidically linked to N-acetylglucosamine; and $R^{10}$ is a disaccharide consisting of galactose glycosidically linked to N-acetylglucosamine.

13. The compound of claim 12 which is 5-(methoxycarbonyl)pentyl 2O-[5-acetamido-3,5-dideoxy-D-glycero-D-galactononulopyranosylonic acid (2→6)-β-D-galactopyranosyl-(1→4)-2-acetamido-2-deoxy-D-glycopyranosyl]-4-O-[β-D-galactopyranosyl-(1→4)-2-acetamido-2-deoxy-D-glucopyranosyl]-β-D-galactopyranoside.

14. A compound comprising the formula VIII

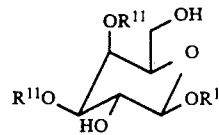

wherein
each $R^{11}$ is independently a monosaccharide selected from the group consisting of glucosamine, N-protected glucosamine, and O-protected glucosamine, or a disaccharide consisting of galactose glycosidically linked to N-acetylglucosamine.

15. The compound of claim 14 which is:

5-(Methoxycarbonyl)pentyl 3,4-di-O-(2-acetamido-2-deoxy-β-D-glucopyranosyl)-β-D-galactopyranoside;

5-(Methoxycarbonyl)pentyl 3,4-di-O-{β-D-galactopyranosyl-(1→4)-2-acetamido-2-deoxy-β-D-glucopyranosyl}-β-D-galactopyranoside.

* * * * *